(12) United States Patent
Nishida

(10) Patent No.: US 12,133,718 B2
(45) Date of Patent: Nov. 5, 2024

(54) BLOOD PRESSURE MEASUREMENT DEVICE

(71) Applicants: OMRON Corporation, Kyoto (JP); OMRON HEALTHCARE Co., Ltd., Kyoto (JP)

(72) Inventor: Tomoyuki Nishida, Kyoto (JP)

(73) Assignees: OMRON CORPORATION, Kyoto (JP); OMRON HEALTHCARE CO., LTD., Kyoto (JP)

( * ) Notice: Subject to any disclaimer, the term of this patent is extended or adjusted under 35 U.S.C. 154(b) by 730 days.

(21) Appl. No.: 17/242,408

(22) Filed: Apr. 28, 2021

(65) Prior Publication Data

US 2021/0244300 A1    Aug. 12, 2021

Related U.S. Application Data

(63) Continuation of application No. PCT/JP2019/043664, filed on Nov. 7, 2019.

(30) Foreign Application Priority Data

Nov. 9, 2018  (JP) ................................ 2018-211648

(51) Int. Cl.
*A61B 5/022* (2006.01)
*A61B 5/00* (2006.01)
(Continued)

(52) U.S. Cl.
CPC ...... *A61B 5/02233* (2013.01); *A61B 5/02141* (2013.01); *A61B 5/0235* (2013.01);
(Continued)

(58) Field of Classification Search
CPC . A61B 5/02233; A61B 5/021; A61B 5/02141; A61B 5/022; A61B 5/02438;
(Continued)

(56) References Cited

U.S. PATENT DOCUMENTS

| | | | |
|---|---|---|---|
| 2005/0182331 A1* | 8/2005 | Millay | A61B 5/02233 600/499 |
| 2006/0135873 A1 | 6/2006 | Karo et al. | |
| 2020/0187799 A1 | 6/2020 | Nishikawa et al. | |

FOREIGN PATENT DOCUMENTS

| | | |
|---|---|---|
| CN | 1792320 | 6/2006 |
| CN | 110049720 | 7/2019 |

(Continued)

OTHER PUBLICATIONS

International Preliminary Report on Patentability issued May 14, 2021 in International (PCT) Patent Application No. PCT/JP2019/043664.

*Primary Examiner* — Matthew Kremer
*Assistant Examiner* — Elina Sohyun Ahn
(74) *Attorney, Agent, or Firm* — Wenderoth, Lind & Ponack, L.L.P.

(57) ABSTRACT

A blood pressure measurement device includes a curler curving in such a manner as to follow along a circumferential direction of the wrist and formed of a first end and a second end spaced apart from each other, and a cuff formed of a resin material, the cuff including one or more bag-like structures stacked on one another and a bonded portion being bonded to the curler, each of the bag-like structures being formed by welding two sheet members and configured to be inflated with a fluid, and the bonded portion being welded to the sheet member disposed on the curler side of the bag-like structure at a position closer to a center of the bag-like structure than edge portions where the two sheet members of the bag-like structure are welded together.

4 Claims, 21 Drawing Sheets

(51) Int. Cl.
*A61B 5/021* (2006.01)
*A61B 5/0235* (2006.01)

(52) U.S. Cl.
CPC ....... *A61B 5/681* (2013.01); *A61B 2560/0214* (2013.01); *A61B 2562/0247* (2013.01)

(58) Field of Classification Search
CPC .................. A61B 5/0235; A61B 5/681; A61B 2560/0214; A61B 2562/0247
See application file for complete search history.

(56) References Cited

FOREIGN PATENT DOCUMENTS

| | | |
|---|---|---|
| EP | 1 671 580 | 6/2006 |
| JP | 61-196705 | 12/1986 |
| JP | 2004-195056 A | 7/2004 |
| JP | 2006-174860 A | 7/2006 |
| JP | 2018-102743 A | 7/2018 |
| JP | 2018-130161 A | 8/2018 |
| KR | 10-2006-0070451 | 6/2006 |

\* cited by examiner

[FIG. 1]
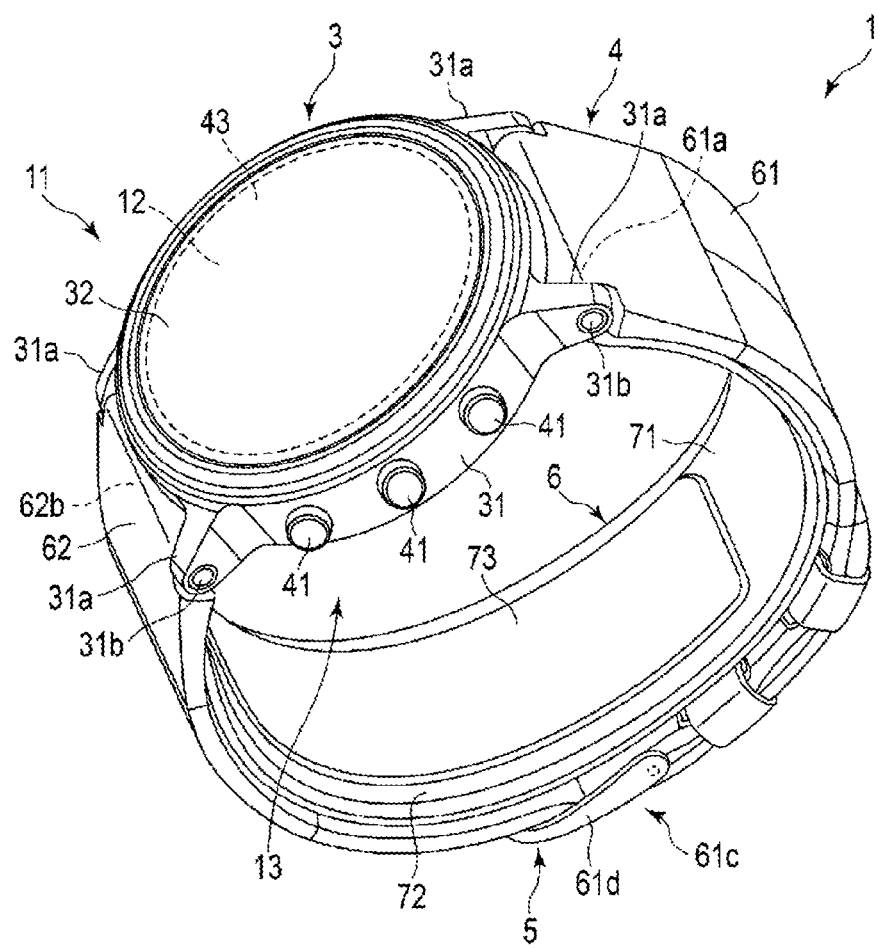

[FIG. 2]
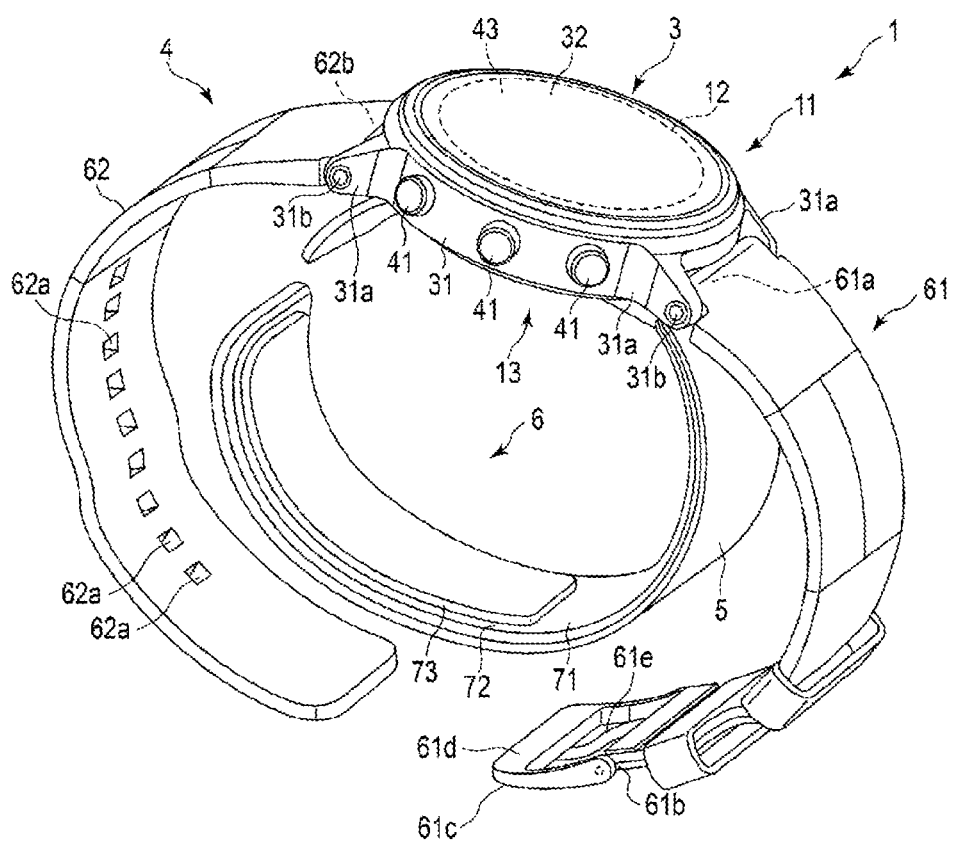

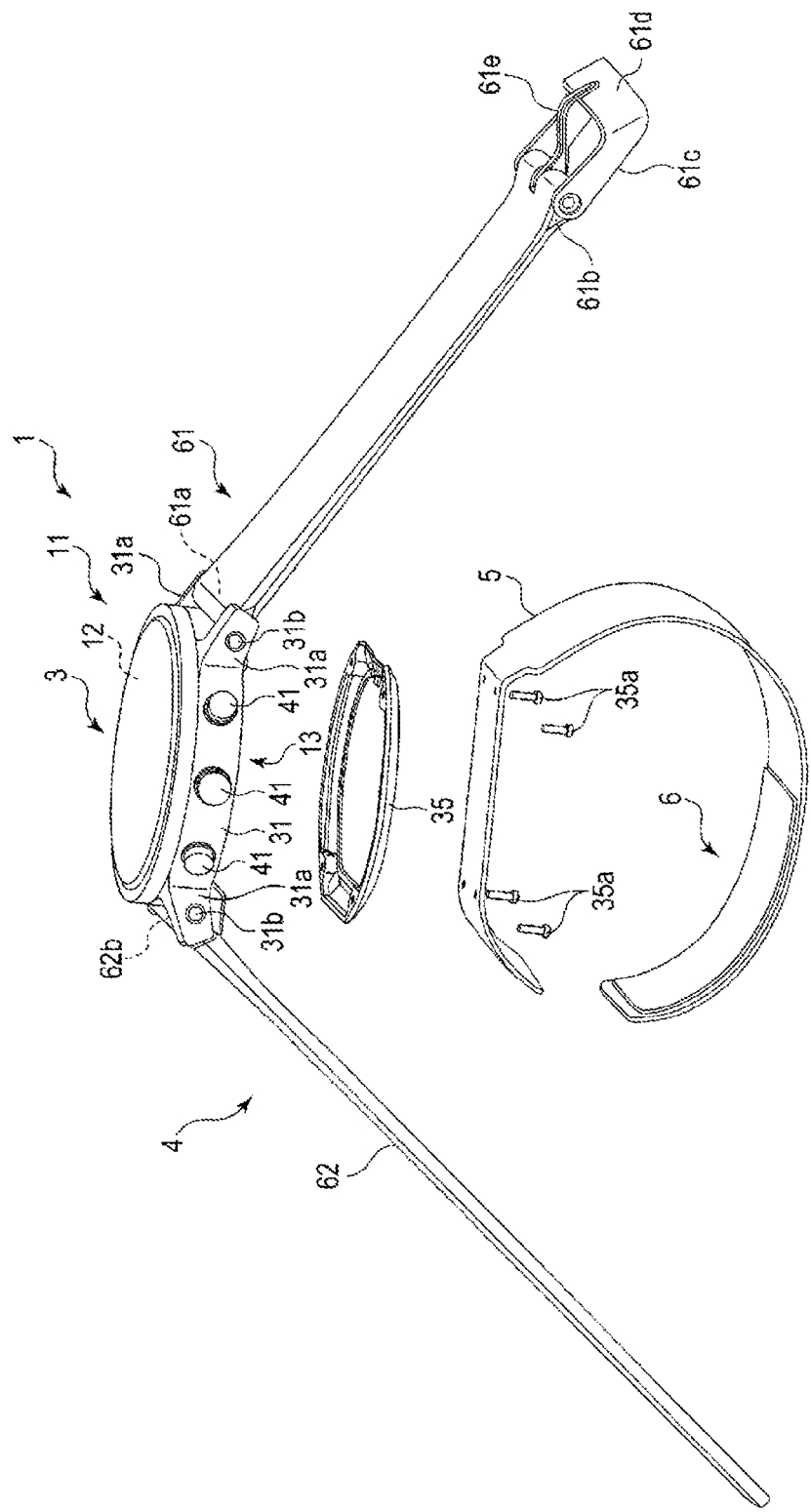
[FIG. 3]

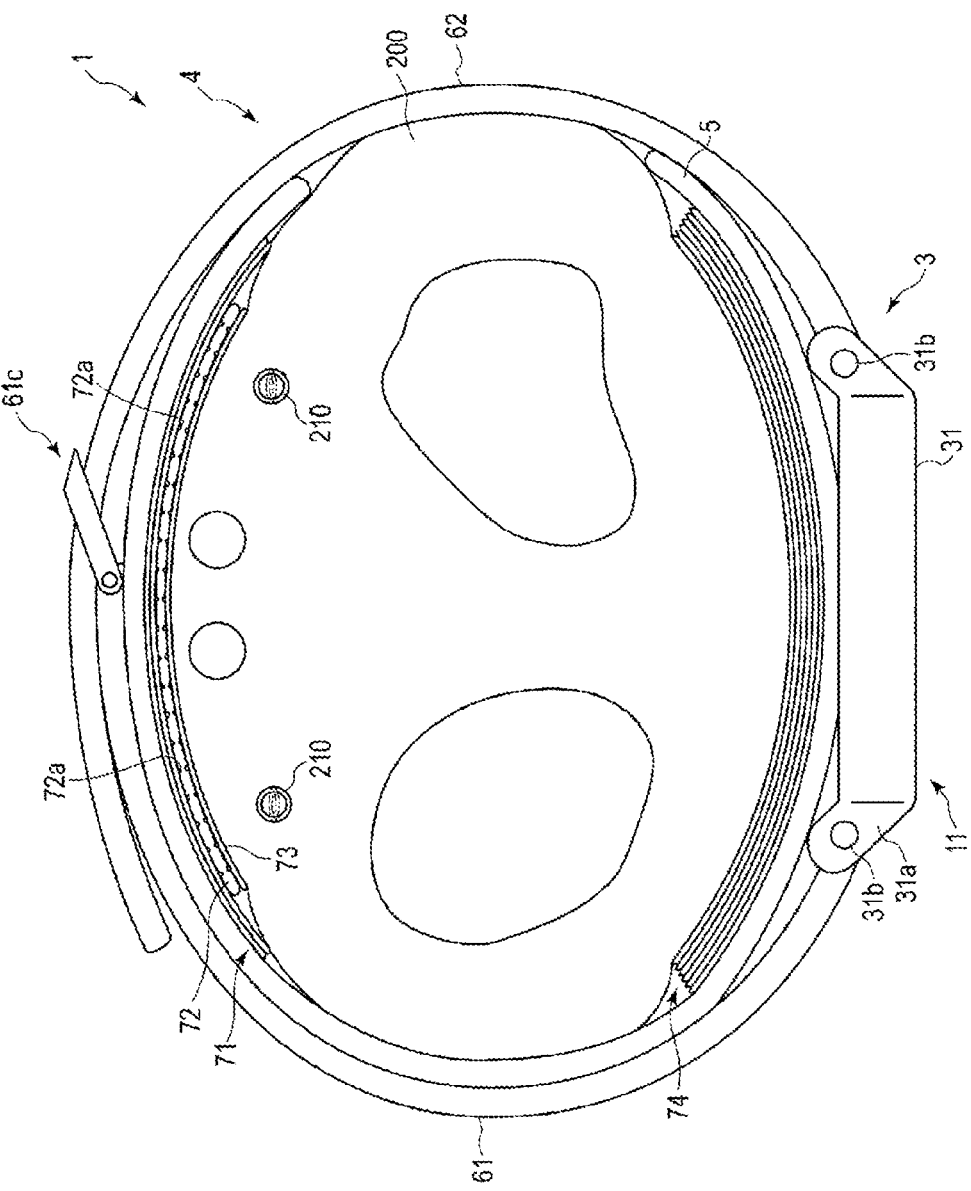
[FIG. 4]

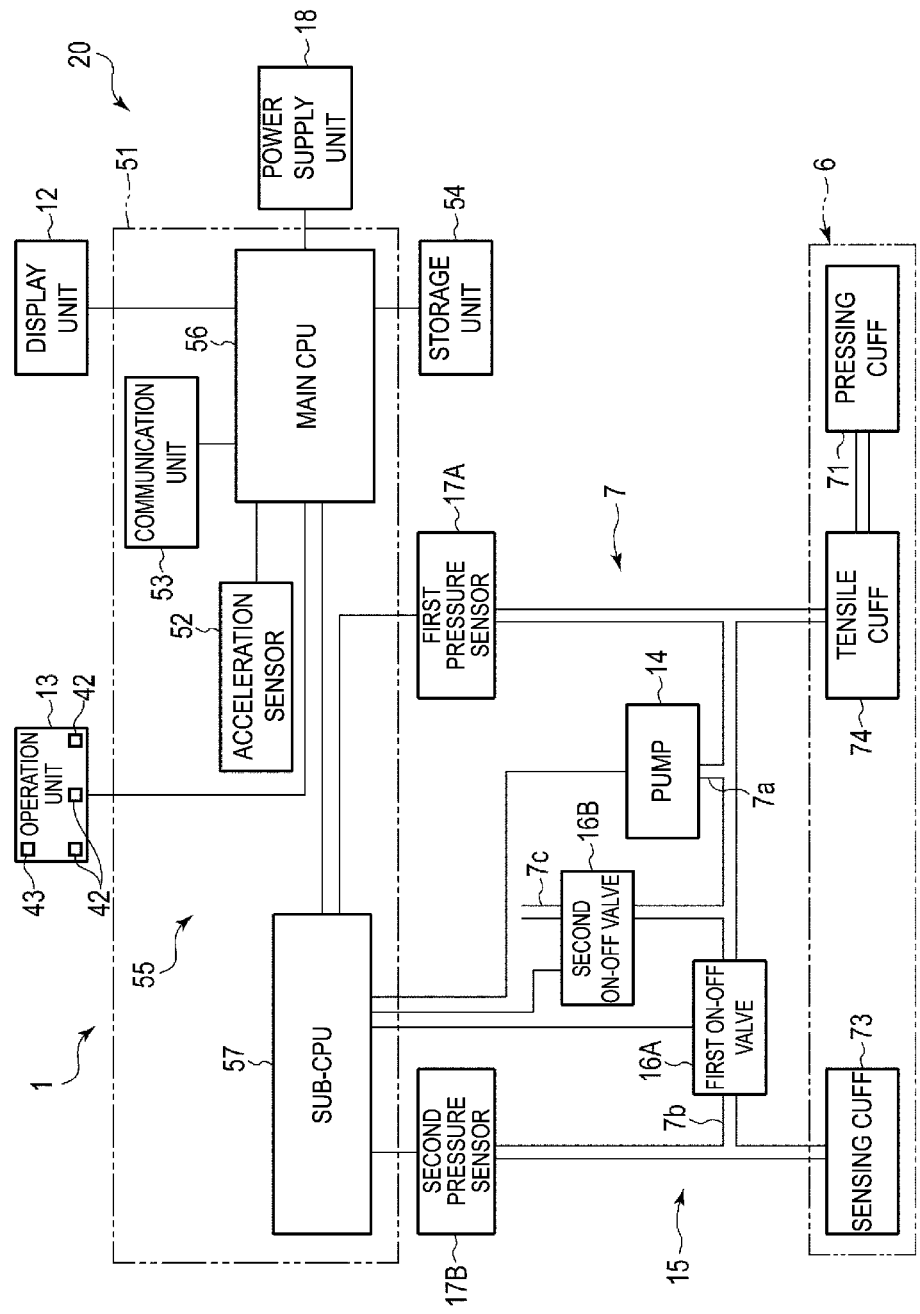

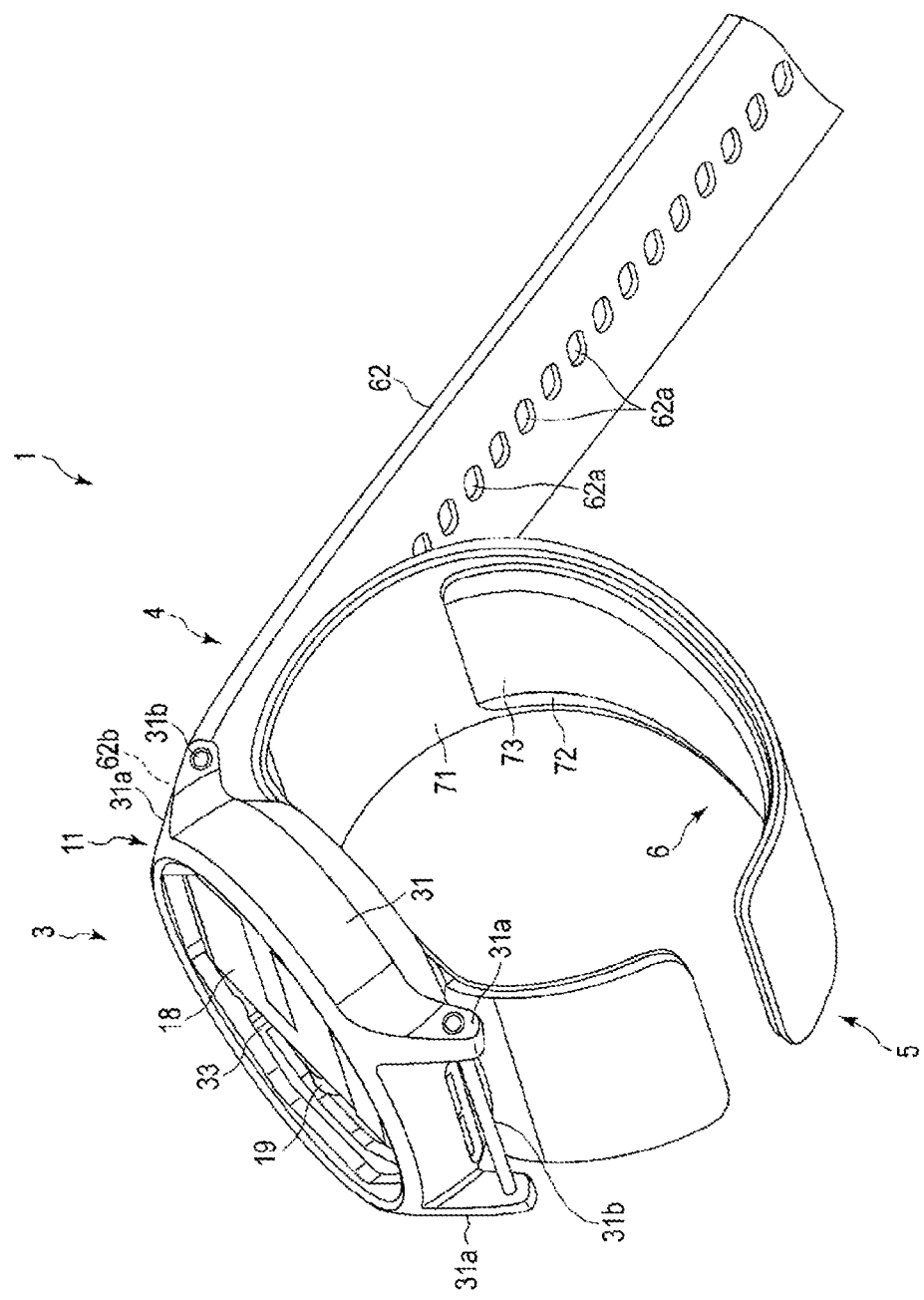
[FIG. 6]

[FIG. 7]
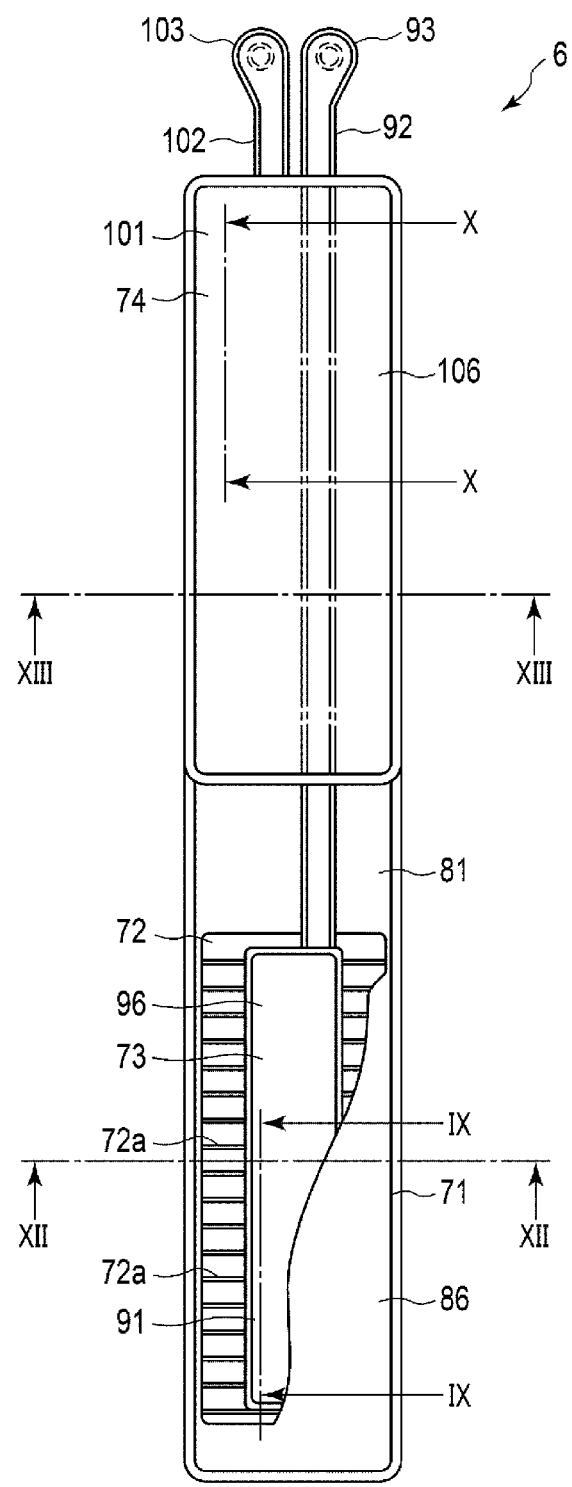

[FIG. 8]
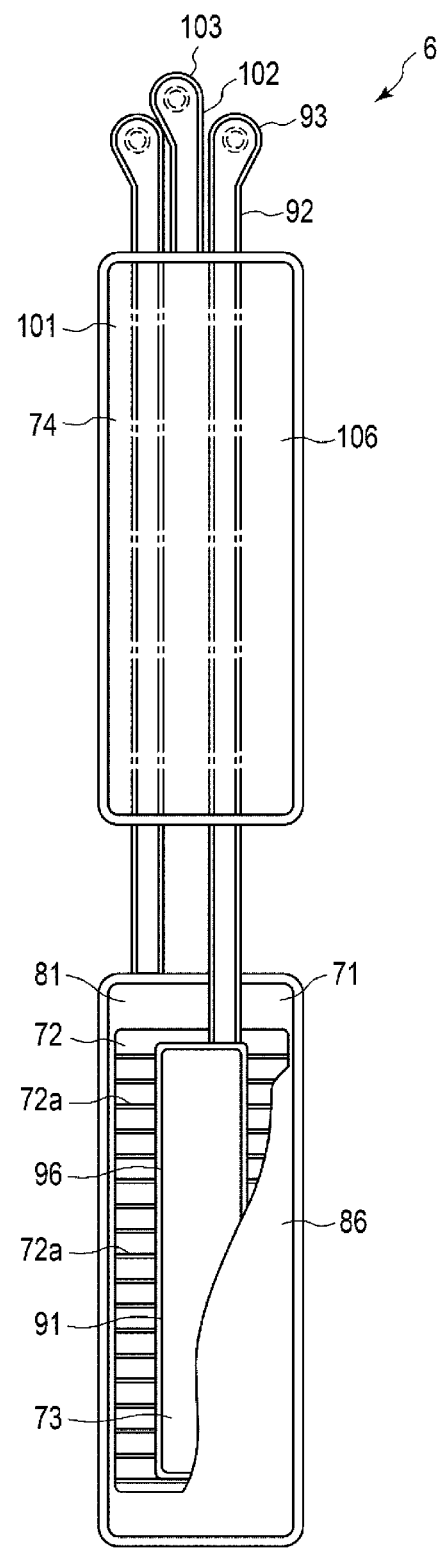

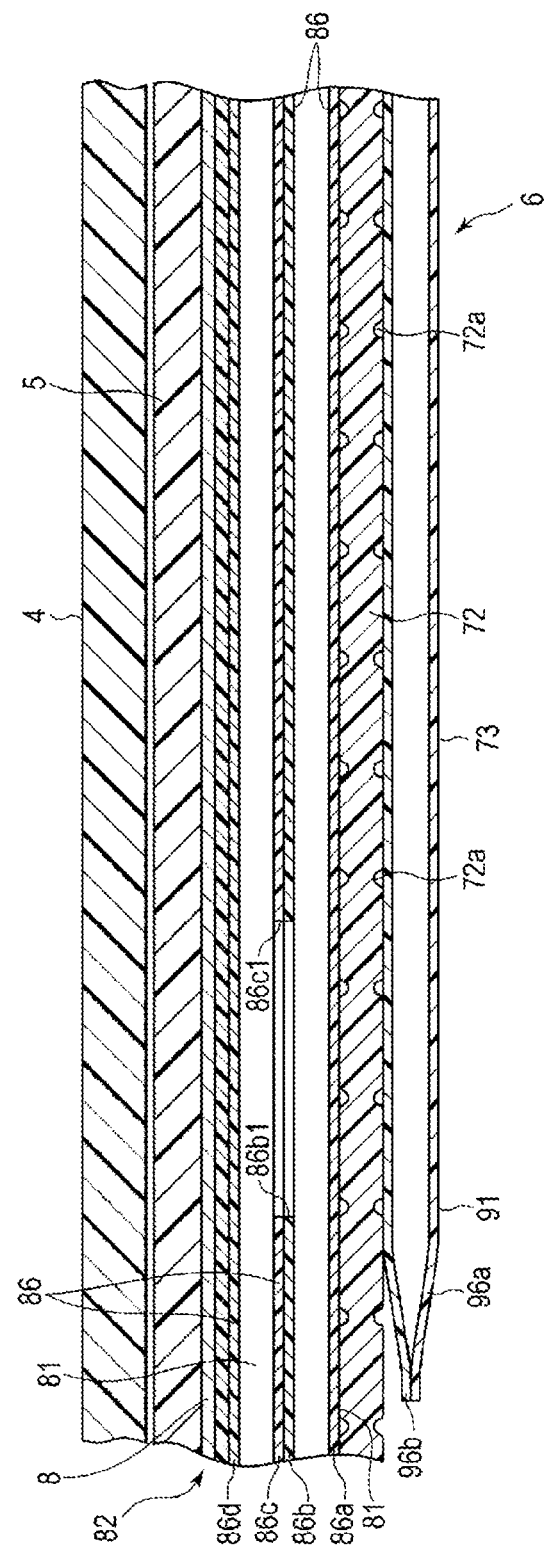
[FIG. 9]

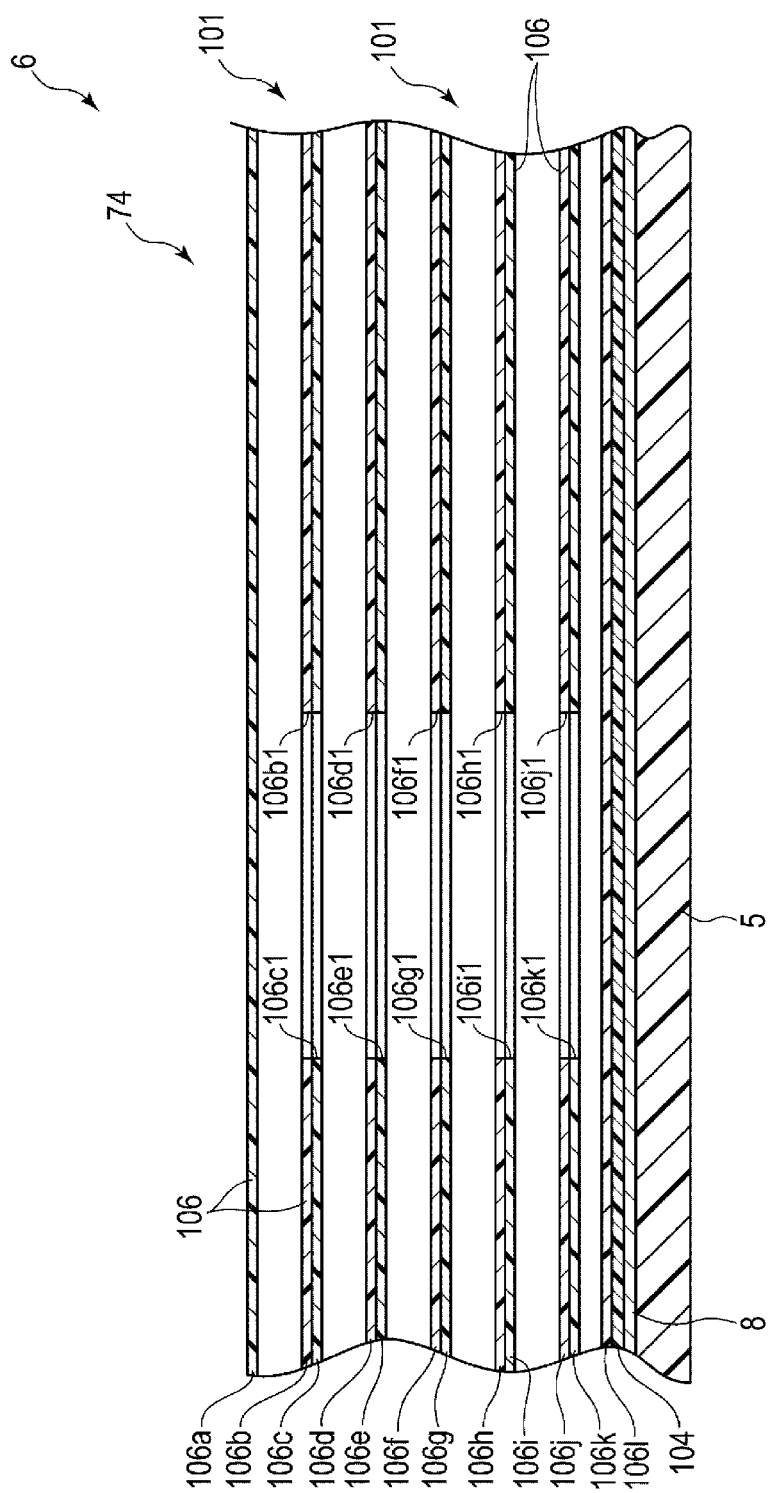
[FIG. 10]

[FIG. 11]
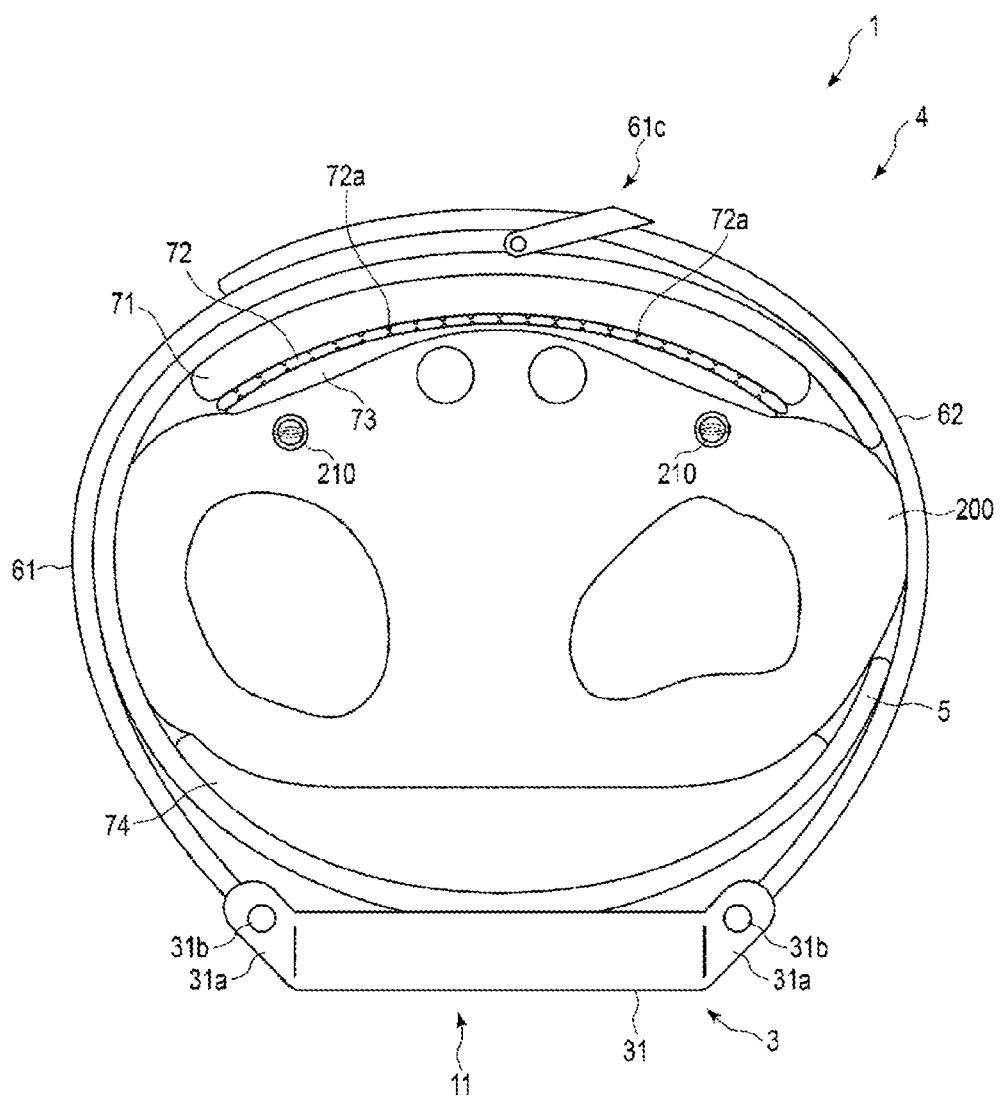

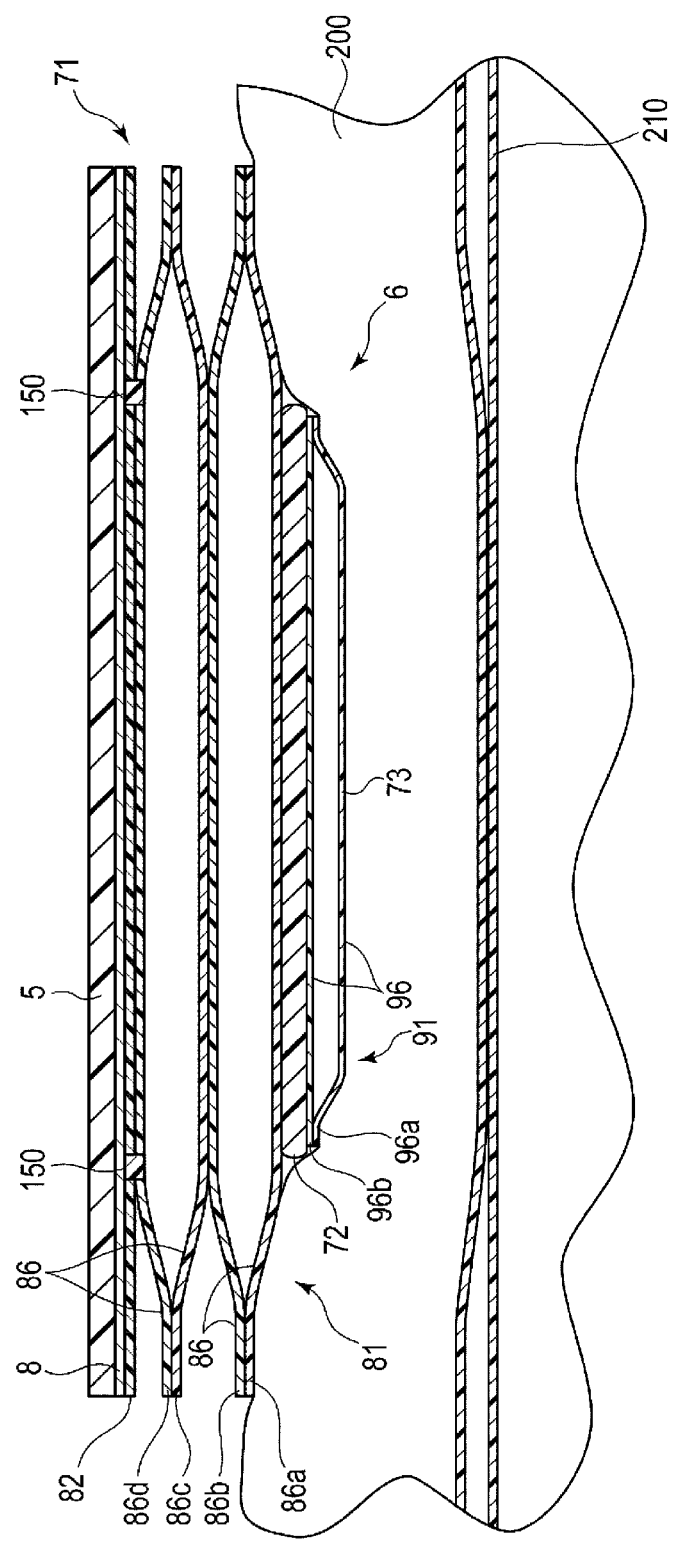

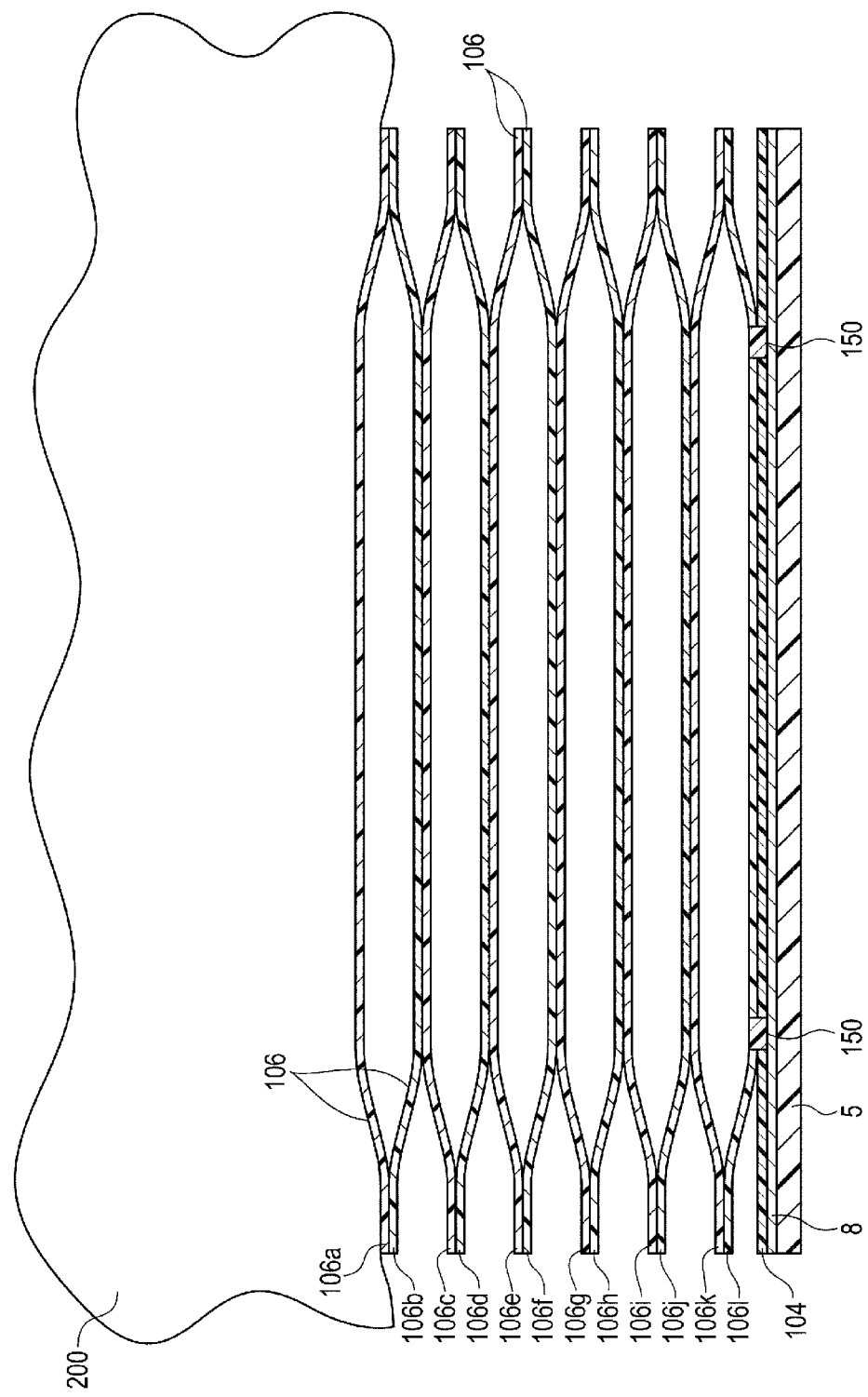

[FIG. 14]
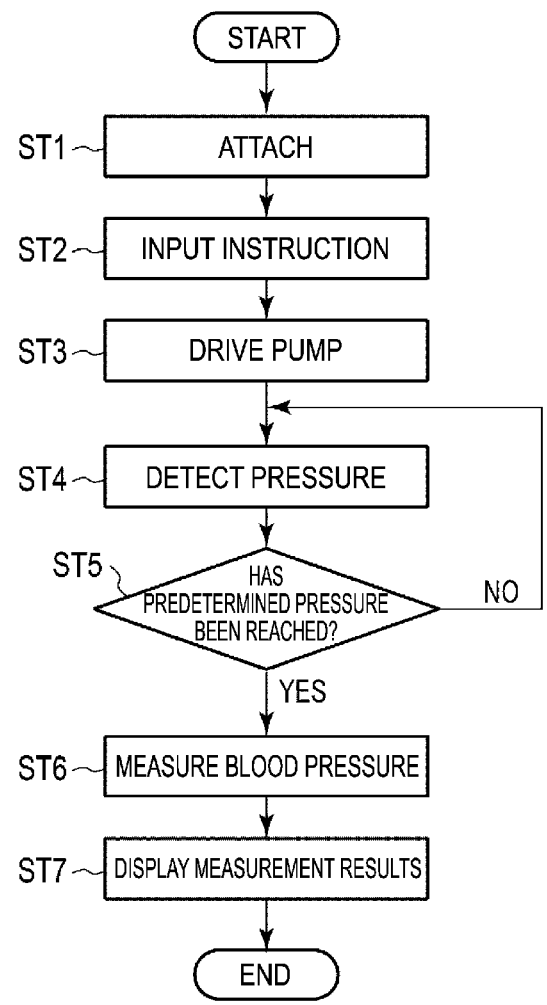

[FIG. 15]
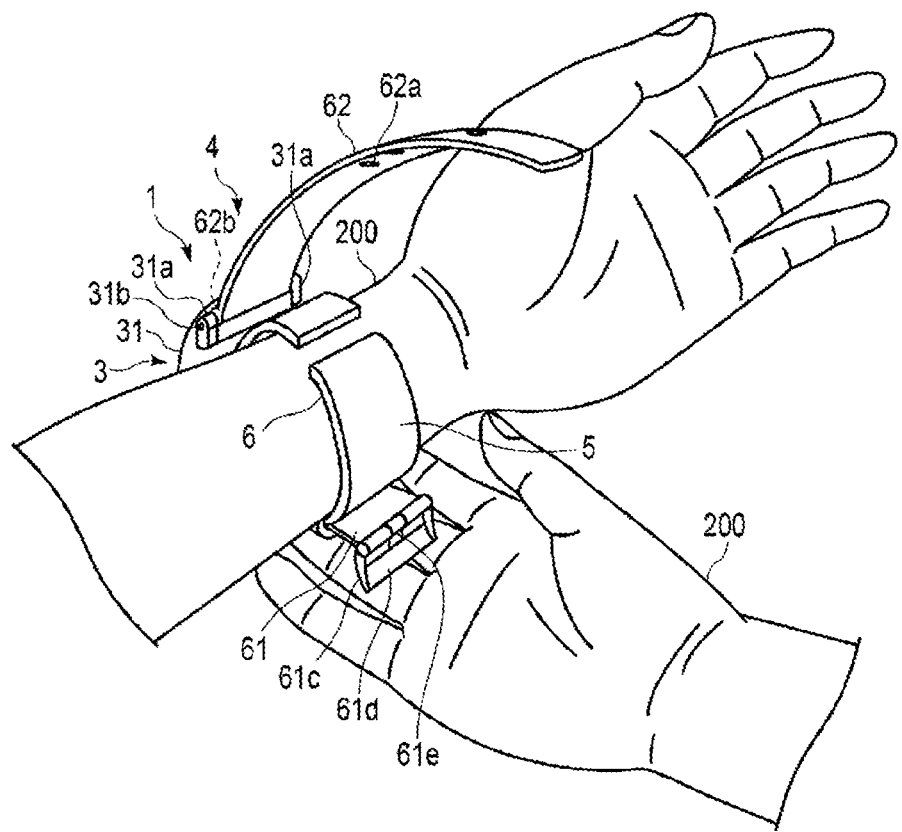

[FIG. 16]
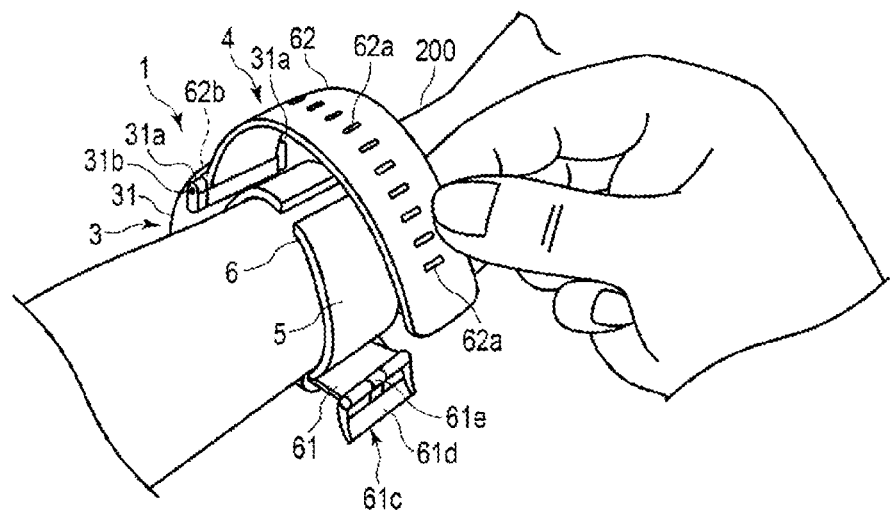
[FIG. 17]
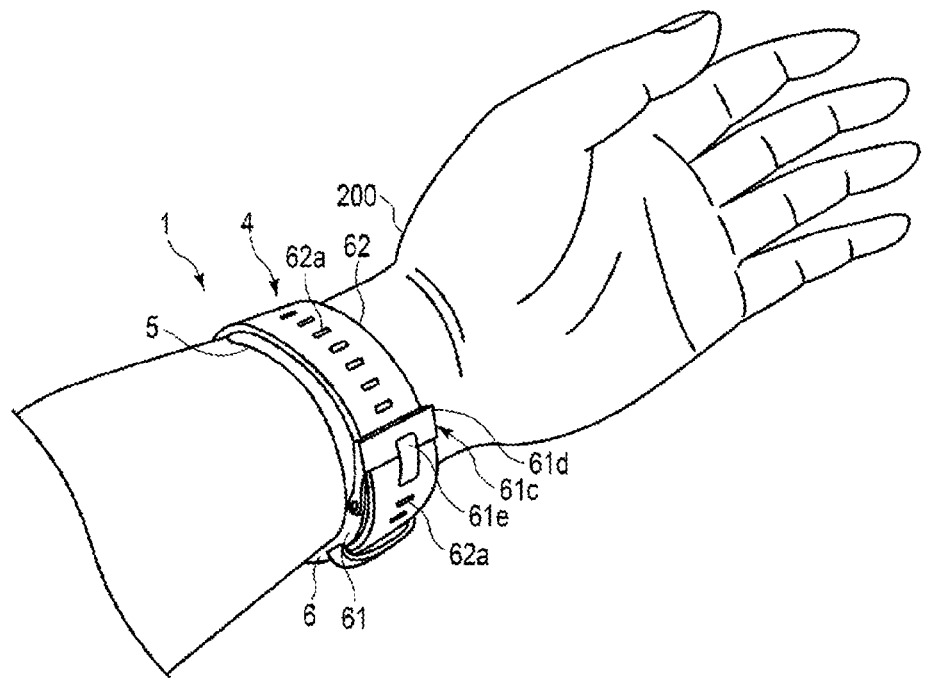

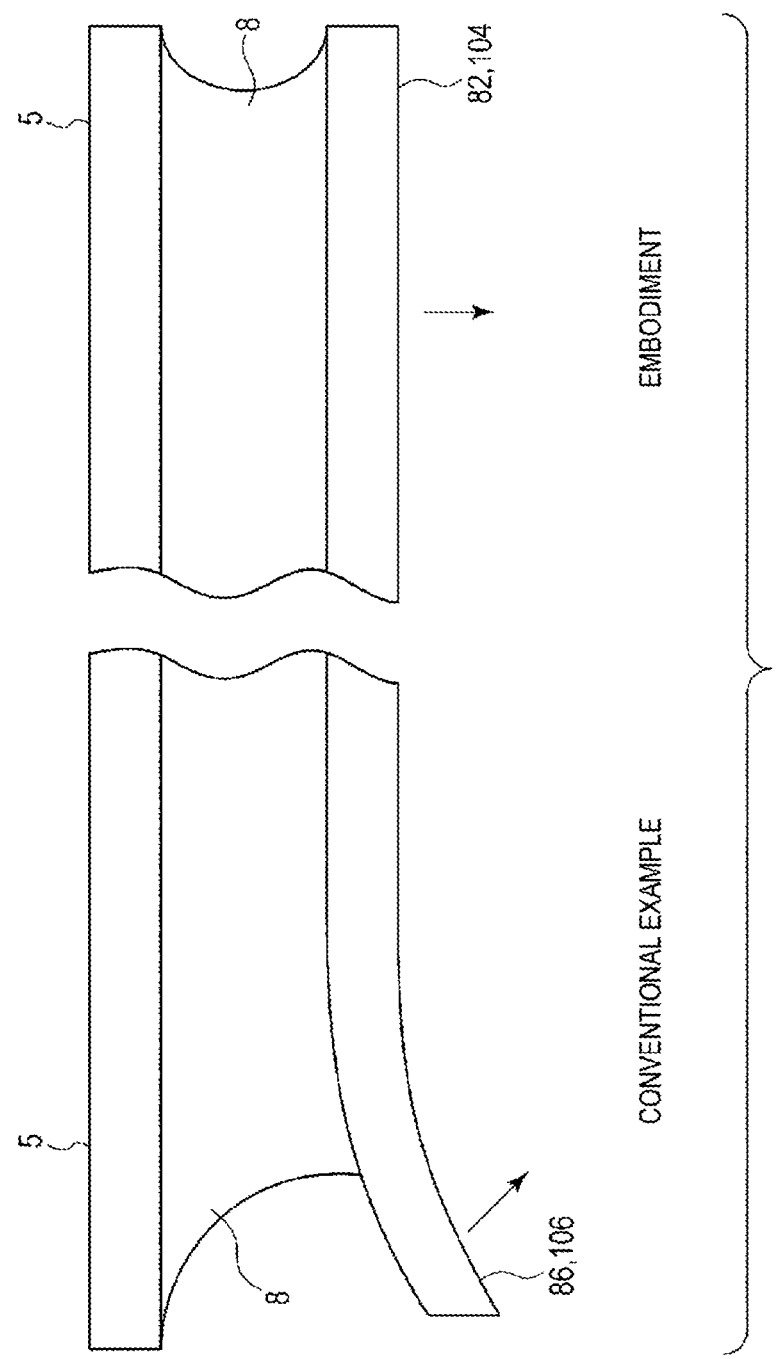

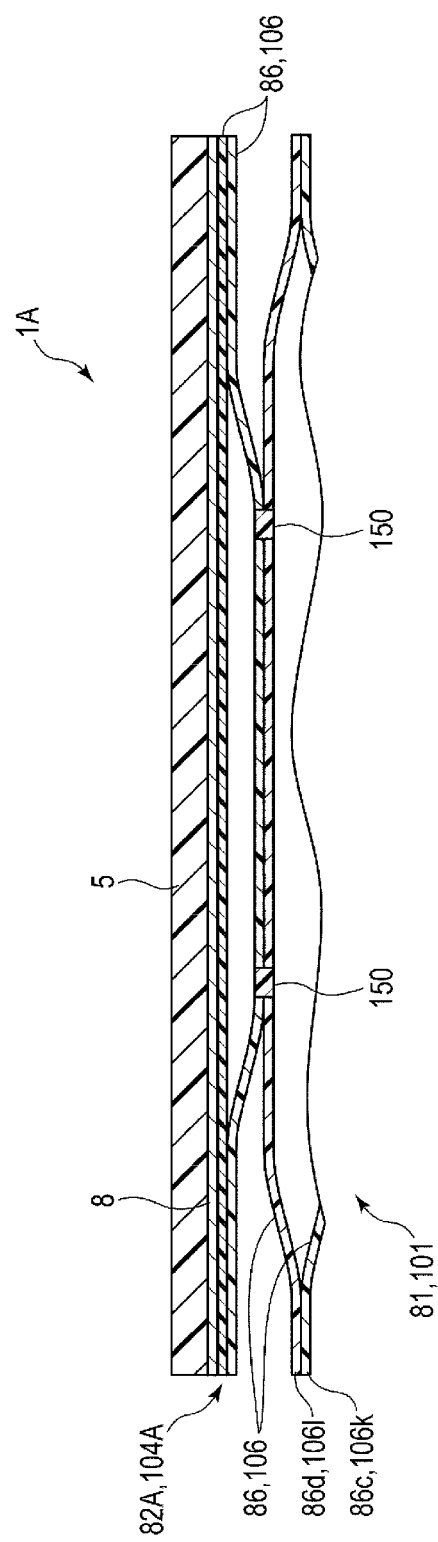

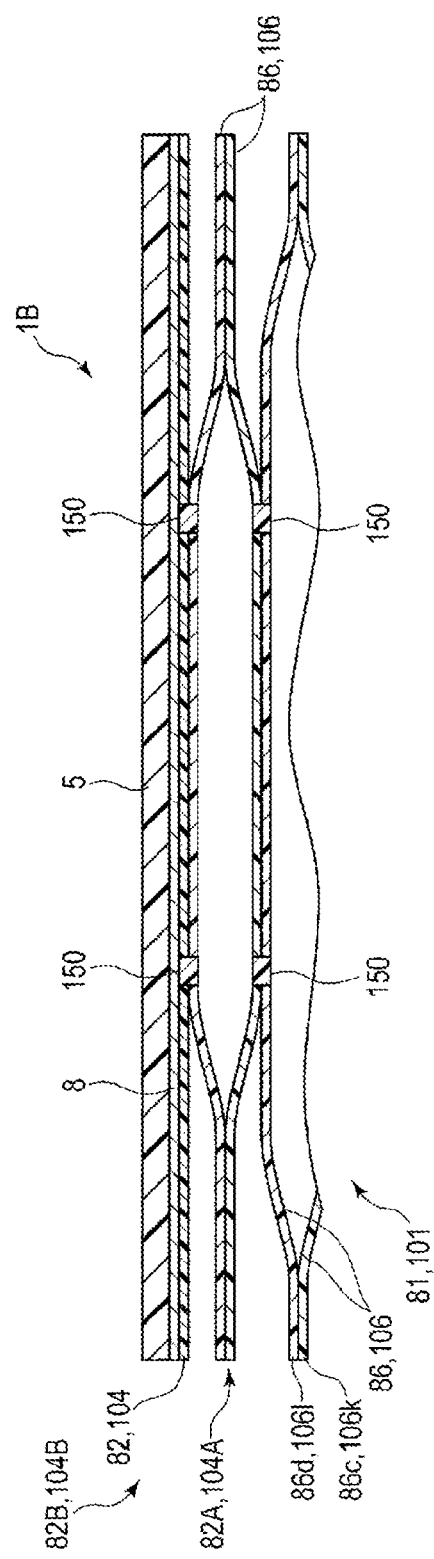

[FIG. 21]
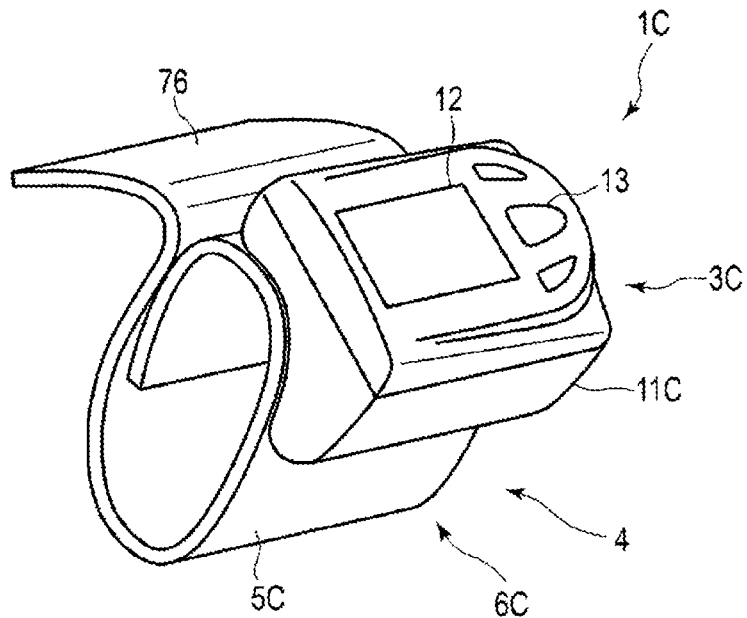
[FIG. 22]
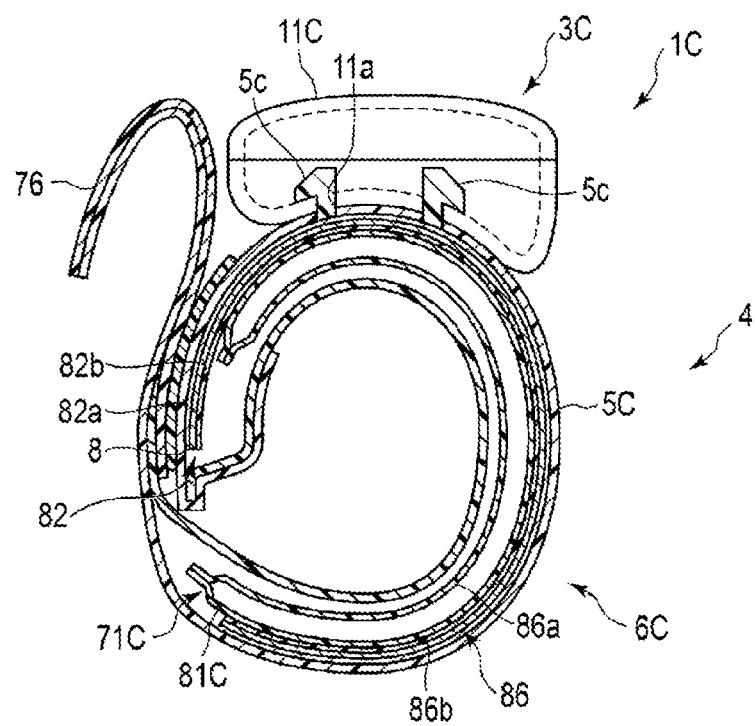

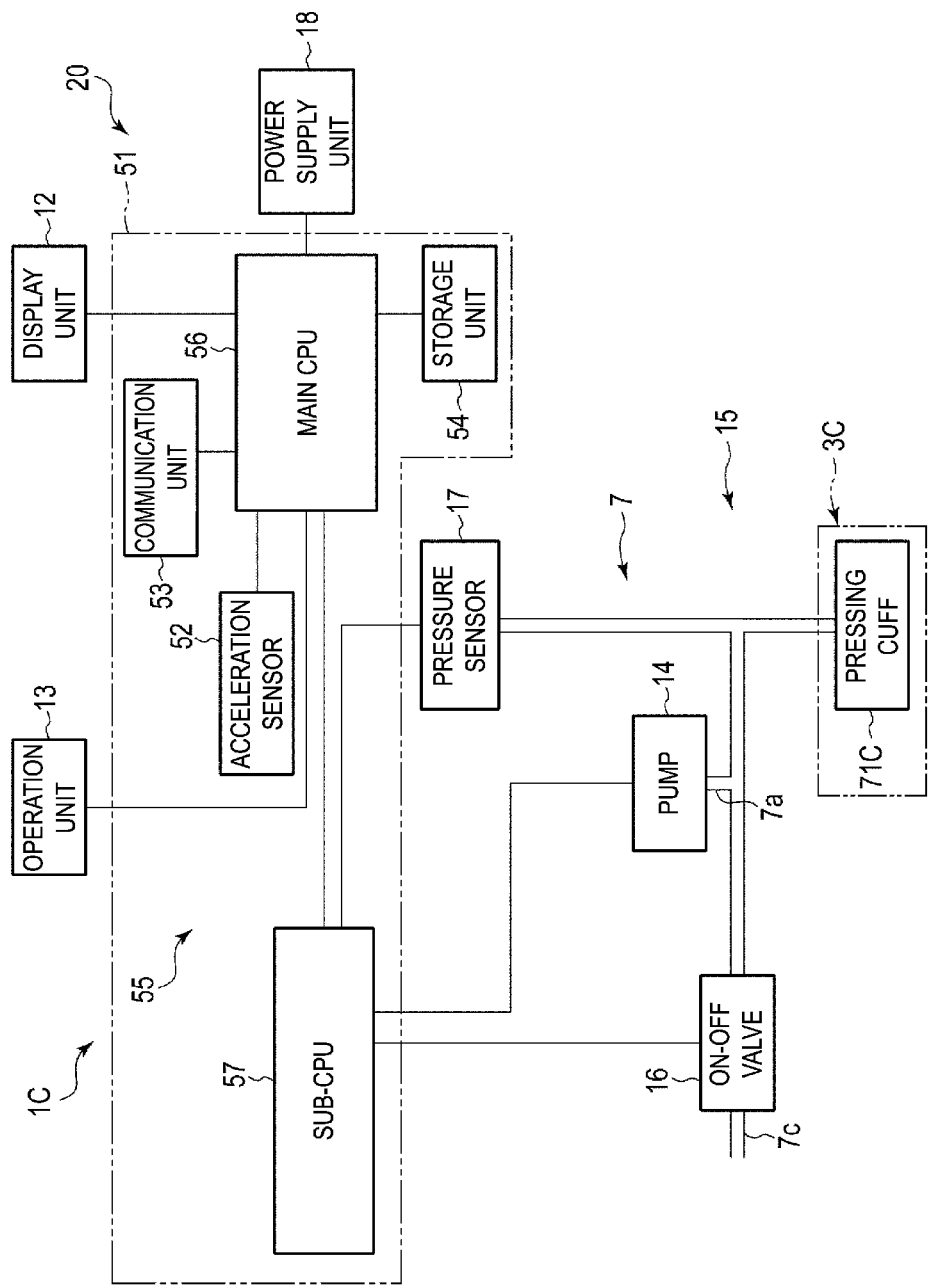
[FIG. 23]

BLOOD PRESSURE MEASUREMENT DEVICE

CROSS-REFERENCE TO RELATED APPLICATIONS

This application is the U.S. national stage application filed pursuant to 35 U.S.C. 365(c) and 120 as a continuation of International Patent Application No. PCT/JP2019/043664, filed Nov. 7, 2019, which application claims priority from Japanese Patent Application No. 2018-211648, filed Nov. 9, 2018, which applications are incorporated herein by reference in their entireties.

TECHNICAL FIELD

The present invention relates to a blood pressure measurement device for measuring blood pressure.

BACKGROUND ART

In recent years, blood pressure measurement devices for measuring blood pressure are being used to monitor health status at home, as well as in medical facilities. A blood pressure measurement device detects vibration of the artery wall to measure blood pressure by, for example, inflating and contracting a cuff wrapped around the upper arm or the wrist of a living body and detecting the pressure of the cuff using a pressure sensor.

As such a blood pressure measurement device, for example, a so-called integral type is known in which a cuff is integrated with a device body feeding a fluid to the cuff. Such blood pressure measurement devices pose a problem in that wrinkles, folds, or the like in the cuff reduce the accuracy of measurement results for the measured blood pressure. Additionally, in the blood pressure measurement device, the cuff needs to be inflated in the direction in which the blood vessels are occluded and to closely contact the wrist.

Thus, JP 2018-102743 A discloses a technique as a blood pressure measurement device in which a curler is used between a belt and the cuff to bring the cuff inflated into close contact with the upper arm or the wrist. In such a blood pressure measurement device, the cuff is bonded and fixed to the curler using a bonding layer such as a double-sided tape, thus integrating the cuff with the curler.

CITATION LIST

Patent Literature

Patent Document 1: JP 2018-102743 A

SUMMARY OF INVENTION

Technical Problem

In the blood pressure measurement device described above, when the cuff is inflated, a central side of the cuff bulges with respect to an edge side of the cuff. When the central side of the cuff bulges with respect to an end portion side of the cuff, stress applied to the bonding layer bonding the cuff to the curler concentrates at the edge side of the cuff. Thus, stress occurs in the bonding layer to peel off the cuff from the curler such that the peel-off originates from the edge side of the cuff. Thus, repeated inflation and contraction of the cuff may lead to peel-off of the cuff from the curler. In particular, reduced widths of the curler and the cuff reduces the area over which the cuff and the curler are bonded, causing the cuff to peel off easily from the curler. Thus, the widths of the cuff and the curler may be increased to increase a bonding area, thus improving the junction strength between the curler and cuff.

However, as the blood pressure measurement device, wearable devices attached to the wrist have recently been proposed, and there has been a demand for further miniaturization. Thus, a technique is required that allows suppression of the peeling between the cuff and the curler without increasing the widths of the cuff and the curler.

Thus, an object of the present invention is to provide a blood pressure measurement device that can suppress the peeling between the cuff and the curler.

Solution to Problem

According to one aspect, a blood pressure measurement device is provided that includes a curler curving in such a manner as to follow along a circumferential direction of the wrist and formed with a first end and a second end spaced apart from each other, and a cuff formed of a resin material, the cuff including one or more bag-like structures stacked on one another and a bonded portion being bonded to the curler, each of the bag-like structures being formed by welding two sheet members, and configured to be inflated with a fluid, and the bonded portion being welded to the sheet member disposed on the curler side of the bag-like structure at a position closer to a center of the bag-like structure than edge portions where the two sheet members of the bag-like structure are welded together.

Here, the fluid includes a liquid and air. The cuff refers to a member that is wrapped around the upper arm, the wrist, or the like of a living body when the blood pressure is measured and that is inflated by being fed with the fluid. The cuff includes a bag-like structure such as an air bag.

According to this aspect, the bonded portion is welded to the sheet member disposed on the curler side of the bag-like structure at the position closer to the center of the bag-like structure than the edge portions where the two sheet members of the bag-like structure are welded together. Accordingly, when the bag-like structure is inflated, stress concentration points generated in the curler and the bonded portion are on the center side of the bonding layer, and thus, tensile stress occurs at the stress concentration points. This allows suppression of the peeling between the cuff and the curler during inflation of the bag-like structure. Additionally, the peeling between the curler and the cuff can be suppressed, allowing the blood pressure measurement device to be miniaturized.

In the blood pressure measurement device according to the one aspect described above, the blood pressure measurement device is provided in which the bonded portion is the sheet member integrally welded to the sheet member disposed on the curler side of the bag-like structure.

Thus, according to this configuration, the configuration may be simplified such that the sheet member is welded to the sheet member disposed on the curler side of the bag-like structure. This enables a reduction in manufacturing costs for the blood pressure measurement device and allows easy manufacturing of the blood pressure measurement device. Additionally, according to this configuration, the dimension of the cuff in the thickness direction is increased only by an amount corresponding to the dimension of the sheet member in the thickness direction, allowing suppression of an increase in the size of the blood pressure measurement device.

In the blood pressure measurement device according to the one aspect, the blood pressure measurement device is provided, in which the bonded portion is formed, by welding two of the sheet members, like a bag configured to be inflated with the fluid into a shape smaller than the bag-like structure, and the bonded portion is integrally welded to the sheet member disposed on the curler side of the bag-like structure.

According to this configuration, the configuration is simplified such that the bonded portion is formed, by welding the two sheet members, like a bag that is inflated into a shape smaller than the bag-like structure. Thus, the blood pressure measurement device can be inexpensively and easily manufactured. In addition, according to this configuration, the dimension of the cuff in the thickness direction is increased only by an amount corresponding to the dimension of the two sheet members in the thickness direction, allowing suppression of an increase in the size of the blood pressure measurement device.

In the blood pressure measurement device according to the one aspect described above, the blood pressure measurement device is provided, in which the bonded portion is formed, by welding the two sheet members, like a bag configured to be inflated into a shape smaller than the bag-like structure, and the bonded portion includes a first bonded portion integrally welded to the sheet member disposed on the curler side of the bag-like structure and a second bonded portion corresponding to the sheet member integrally welded to the sheet member disposed on the curler side of the first bonded portion.

According to this configuration, the configuration may be simplified such that by welding the two sheet members, the first bonded portion in the bag shape, which is inflated into a shape smaller than the bag-like structure, and the second bonded portion corresponding to the sheet member are welded to the sheet member disposed on the curler side of the bag-like structure. Thus, the blood pressure measurement device may have a simple configuration including one additional sheet member and an additional one-layer bag-like structure with an enlarged junction margin, and can be inexpensively and easily manufactured. Additionally, according to this configuration, the dimension of the cuff in the thickness direction is increased only by an amount corresponding to the dimension of three sheet members in the thickness direction, allowing suppression of an increase in the size of the blood pressure measurement device.

In the blood pressure measurement device according to the one aspect described above, the blood pressure measurement device is provided, in which the bonded portion has a higher bending stress than the sheet member.

According to this aspect, the cuff includes the bonded portion having a higher bending strength than the bag-like structure, and the bonded portion is bonded to the curler, and thus even when the bag-like structure is inflated and thus deformed, deformation of the bonded portion is suppressed. Accordingly, stress occurring in the bonding layer between the curler and the bonded portion is stress in a tensile direction. Thus, the blood pressure measurement device can more properly suppress the peeling between the curler and the cuff.

Advantageous Effects of Invention

The present invention can provide a blood pressure measurement device that can suppress the peeling between the curler and the cuff.

BRIEF DESCRIPTION OF DRAWINGS

FIG. 1 is a perspective view illustrating a configuration of a blood pressure measurement device according to a first embodiment of the present invention.

FIG. 2 is a perspective view illustrating the configuration of the blood pressure measurement device.

FIG. 3 is an exploded view illustrating the configuration of the blood pressure measurement device.

FIG. 4 is an explanatory diagram illustrating a state in which the blood pressure measurement device is attached to the wrist.

FIG. 5 is a block diagram illustrating the configuration of the blood pressure measurement device.

FIG. 6 is a perspective view illustrating a configuration of a device body and a curler of the blood pressure measurement device.

FIG. 7 is a plan view illustrating a configuration of a cuff structure of the blood pressure measurement device.

FIG. 8 is a plan view illustrating another configuration of the cuff structure of the blood pressure measurement device.

FIG. 9 is a cross-sectional view illustrating a configuration of a belt, the curler, and the cuff structure of the blood pressure measurement device.

FIG. 10 is a cross-sectional view illustrating the configuration of the curler and the cuff structure of the blood pressure measurement device.

FIG. 11 is an explanatory diagram illustrating the configuration in which the cuff structure is inflated in a state in which the blood pressure measurement device attached to the wrist.

FIG. 12 is a cross-sectional view illustrating the configuration in which the cuff structure is inflated in a state in which the blood pressure measurement device attached to the wrist.

FIG. 13 is a cross-sectional view illustrating the configuration in which the cuff structure is inflated in a state in which the blood pressure measurement device is attached to the wrist.

FIG. 14 is a flowchart illustrating an example of usage of the blood pressure measurement device.

FIG. 15 is a perspective view illustrating an example in which the blood pressure measurement device is attached to the wrist.

FIG. 16 is a perspective view illustrating an example in which the blood pressure measurement device is attached to the wrist.

FIG. 17 is a perspective view illustrating an example in which the blood pressure measurement device is attached to the wrist.

FIG. 18 is an explanatory diagram illustrating stress applied to the cuff of the blood pressure measurement device in comparison to the stress in a conventional example.

FIG. 19 is a cross-sectional view illustrating a configuration of a curler and a cuff structure of a blood pressure measurement device according to a second embodiment of the present invention.

FIG. 20 is a cross-sectional view illustrating a configuration of a curler and a cuff structure of a blood pressure measurement device according to a third embodiment of the present invention.

FIG. 21 is a perspective view illustrating a configuration of a blood pressure measurement device according to a fourth embodiment of the present invention.

FIG. 22 is a cross-sectional view illustrating the configuration of the blood pressure measurement device.

FIG. 23 is a block diagram illustrating the configuration of the blood pressure measurement device.

DESCRIPTION OF EMBODIMENTS

First Embodiment

An example of a blood pressure measurement device 1 according to a first embodiment of the present invention will be described below with reference to FIGS. 1 to 13.

FIG. 1 is a perspective view illustrating a configuration of the blood pressure measurement device 1 according to an embodiment of the present invention in a state in which a belt 4 is closed. FIG. 2 is a perspective view illustrating the configuration of the blood pressure measurement device 1 in a state in which the belt 4 is open. FIG. 3 is an exploded view illustrating the configuration of the blood pressure measurement device 1. FIG. 4 is an explanatory diagram illustrating a state in which the blood pressure measurement device 1 is attached to the wrist 200. FIG. 5 is a block diagram illustrating the configuration of the blood pressure measurement device 1. FIG. 6 is a perspective view illustrating a configuration of a device body 3 and a curler 5 of the blood pressure measurement device 1. FIG. 7 is a plan view illustrating a configuration of a cuff structure 6 of the blood pressure measurement device 1. FIG. 8 is a plan view illustrating another configuration of the cuff structure 6 of the blood pressure measurement device 1. FIG. 9 is a cross-sectional view illustrating a configuration of the belt 4, the curler 5, and the cuff structure 6 on a palm-side cuff 71 side of the blood pressure measurement device 1, which is taken along line IX-IX in FIG. 7. FIG. 10 is a cross-sectional view illustrating a configuration of the curler 5 and the cuff structure 6 on a back-side cuff 74 side of the blood pressure measurement device 1, which is taken along line X-X in FIG. 7. FIG. 11 is an explanatory diagram illustrating the configuration in which the cuff structure 6 is inflated in a state in which the blood pressure measurement device 1 attached to the wrist 200. FIG. 12 is a cross-sectional view illustrating the configuration in which the cuff structure 6 is inflated in a state in which the blood pressure measurement device 1 attached to the wrist 200, which is taken along line XII-XII in FIG. 7. FIG. 13 is a cross-sectional view illustrating a configuration of the cuff structure 6 with the curler 5 and a tube 92 omitted, on the back-side cuff 74 side of the blood pressure measurement device 1, which is taken along line XIII-XIII in FIG. 7.

The blood pressure measurement device 1 is an electronic blood pressure measurement device attached to a living body. The present embodiment will be described using an electronic blood pressure measurement device having an aspect of a wearable device attached to a wrist 200 of the living body.

As illustrated in FIGS. 1 to 3, the blood pressure measurement device 1 includes a device body 3, a belt 4 that fixes the device body 3 at the wrist, a curler 5 disposed between the belt 4 and the wrist, a cuff structure 6 including a palm-side cuff 71, a sensing cuff 73, and a back-side cuff 74, and a fluid circuit 7 fluidly connecting the device body 3 and the cuff structure 6.

As illustrated in FIGS. 1 to 5, the device body 3 includes, for example, a case 11, a display unit 12, an operation unit 13, a pump 14, a flow path unit 15, an on-off valve 16, a pressure sensor 17, a power supply unit 18, a vibration motor 19, and a control substrate 20. The device body 3 feeds a fluid to the cuff structure 6 using the pump 14, the on-off valve 16, the pressure sensor 17, the control substrate 20, and the like.

As illustrated in FIGS. 1 to 3, the case 11 includes an outer case 31, a windshield 32 that covers an upper opening of the outer case 31, a base 33 provided at a lower portion of an interior of the outer case 31, and a back lid 35 covering a lower portion of the outer case 31.

The outer case 31 is formed in a cylindrical shape. The outer case 31 includes pairs of lugs 31a provided at respective symmetrical positions in the circumferential direction of an outer circumferential surface, and spring rods 31b each provided between the lugs 31 of each of the two pairs of lugs 31a. The windshield 32 is, for example, a circular glass plate.

The base portion 33 holds the display unit 12, the operation unit 13, the pump 14, the on-off valve 16, the pressure sensor 17, the power supply unit 18, the vibration motor 19, and the control substrate 20. Additionally, the base 33 constitutes a portion of the flow path unit 15 that makes the pump 14 and the cuff structure 6 fluidly continuous.

The back lid 35 covers a living body side end portion of the outer case 31. The back lid 35 is fixed to the living body side end portion of the outer case 31 or the base 33 using, for example, four screws 35a or the like.

The display unit 12 is disposed on the base portion 33 of the outer case 31 and directly below the windshield 32. The display unit 12 is electrically connected to the control substrate 20. The display unit 12 is, for example, a liquid crystal display or an organic electroluminescence display. The display unit 12 displays various types of information including the date and time and measurement results of blood pressure values such as the systolic blood pressure and diastolic blood pressure, heart rate, and the like.

The operation unit 13 is configured to be capable of receiving an instruction input from a user. For example, the operation unit 13 includes a plurality of buttons 41 provided on the case 11, a sensor 42 that detects operation of the buttons 41, and a touch panel 43 provided on the display unit 12 or the windshield 32. When operated by the user, the operation unit 13 converts an instruction into an electrical signal. The sensor 42 and the touch panel 43 are electrically connected to the control substrate 20 to output electrical signals to the control substrate 20.

As the plurality of buttons 41, for example, three buttons are provided. The buttons 41 are supported by the base 33 and protrude from the outer circumferential surface of the outer case 31. The plurality of buttons 41 and a plurality of the sensors 42 are supported by the base 33. The touch panel 43 is integrally provided on the windshield 32, for example.

The pump 14 is, for example, a piezoelectric pump. The pump 14 compresses air and feeds compressed air to the cuff structure 6 through the flow path unit 15. The pump 14 is electrically connected to the control substrate 20.

The flow path unit 15 constitutes a flow path connecting from the pump 14 to the palm-side cuff 71 and the back-side cuff 74 and a flow path connecting from the pump 14 to the sensing cuff 73, as illustrated in FIG. 5. Additionally, the flow path unit 15 constitutes a flow path connecting from the palm-side cuff 71 and the back-side cuff 74 to the atmosphere, and a flow path connecting from the sensing cuff 73 to the atmosphere. The flow path unit 15 is a flow path of air constituted by a hollow portion, a groove, a tube, or the like provided in the base portion 33 and the like.

The on-off valve 16 opens and closes a portion of the flow path 15. A plurality of the on-off valves 16 is provided, for example, as illustrated in FIG. 5, and selectively opens and closes the flow path connecting from the pump 14 to the palm-side cuff 71 and the back-side cuff 74, the flow path connecting from the pump 14 to the sensing cuff 73, the flow path connecting from the palm-side cuff 71 and the back-side cuff 74 to the atmosphere, and the flow path connecting from the sensing cuff 73 to the atmosphere, by the combination of opening and closing of each of the on-off valves 16. For example, two on-off valves 16 are used.

The pressure sensor 17 detects the pressures in the palm-side cuff 71, the sensing cuff 73 and the back-side cuff 74. The pressure sensor 17 is electrically connected to the control substrate 20. The pressure sensor 17 converts a detected pressure into an electrical signal, and outputs the electrical signal to the control substrate 20. The pressure sensor 17 is provided in the flow path connecting from the pump 14 to the palm-side cuff 71 and the back-side cuff 74 and in the flow path connecting from the pump 14 to the sensing cuff 73, as illustrated in FIG. 5. These flow paths are continuous through the palm-side cuff 71, the sensing cuff 73, and the back-side cuff 74, and thus the pressure in these flow paths corresponds to the pressure in the internal space of the palm-side cuff 71, the sensing cuff 73, and the back-side cuff 74.

The power supply unit 18 is, for example, a secondary battery such as a lithium ion battery. The power supply unit 18 is electrically connected to the control substrate 20. The power supply unit 18 supplies power to the control substrate 20.

As illustrated in FIGS. 5 and 6, the control substrate 20 includes, for example, a substrate 51, an acceleration sensor 52, a communication unit 53, a storage unit 54, and a control unit 55. The control substrate 20 is constituted by the acceleration sensor 52, the communication unit 53, the storage unit 54, and the control unit 55 that are mounted on the substrate 51.

The substrate 51 is fixed to the base 33 of the case 11 using screws or the like.

The acceleration sensor 52 is, for example, a 3-axis acceleration sensor. The acceleration sensor 52 outputs, to the control unit 55, an acceleration signal representing acceleration of the device body 3 in three directions orthogonal to one another. For example, the acceleration sensor 52 is used to measure, from the detected acceleration, the amount of activity of a living body to which the blood pressure measurement device 1 is attached.

The communication unit 53 is configured to be able to transmit and receive information to and from an external device wirelessly or by wire. For example, the communication unit 53 transmits information controlled by the control unit 55, and information of a measured blood pressure value, a pulse, and the like to an external device via a network, and receives a program or the like for software update from an external device via a network and sends the program or the like to the control unit 55.

In the present embodiment, the network is, for example, the Internet, but is not limited to this. The network may be a network such as a Local Area Network (LAN) provided in a hospital or may be direct communication with an external device using a cable or the like including a terminal of a predetermined standard such as a USB. Thus, the communication unit 53 may be configured to include a plurality of wireless antennas, micro-USB connectors, or the like.

The storage unit 54 pre-stores program data for controlling the overall blood pressure measurement device 1 and a fluid circuit 7, settings data for setting various functions of the blood pressure measurement device 1, calculation data for calculating a blood pressure value and a pulse from pressure measured by the pressure sensors 17, and the like. Additionally, the storage unit 54 stores information such as a measured blood pressure value and a measured pulse.

The control unit 55 is constituted by one or more CPUs, and controls operation of the overall blood pressure measurement device 1 and operation of the fluid circuit. The control unit 55 is electrically connected to and supplies power to the display unit 12, the operation unit 13, the pump 14, each of the on-off valves 16 and the pressure sensors 17.

Additionally, the control unit 55 controls operation of the display unit 12, the pump 14, and the on-off valves 16, based on electrical signals output by the operation unit 13 and the pressure sensors 17.

For example, as illustrated in FIG. 5, the control unit 55 includes a main Central Processing Unit (CPU) 56 that controls operation of the overall blood pressure measurement device 1, and a sub-CPU 57 that controls operation of the fluid circuit 7. For example, the main CPU 56 obtains measurement results such as blood pressure values, for example, the systolic blood pressure and the diastolic blood pressure, and the heart rate, from electrical signals output by the pressure sensor 17, and outputs an image signal corresponding to the measurement results to the display unit 12.

For example, the sub-CPU 57 drives the pump 14 and the on-off valves 16 to feed compressed air to the palm-side cuff 71 and the sensing cuff 73 when an instruction to measure the blood pressure is input from the operation unit 13.

In addition, the sub-CPU 57 controls driving and stopping of the pump 14 and opening and closing of the on-off valves 16 based on electrical signal output by the pressure sensors 17. The sub-CPU 57 controls the pump 14 and the on-off valves 16 to selectively feed compressed air to the palm-side cuff 71 and the sensing cuff 73 and selectively depressurize the palm-side cuff 71 and the sensing cuff 73.

As illustrated in FIGS. 1 to 3, the belt 4 includes a first belt 61 provided on a first pair of lugs 31a and a first spring rod 31b, and a second belt 62 provided on a second pair of lugs 31a and a second spring rod 31b. The belt 4 is wrapped around the wrist 200 with a curler 5 in between.

The first belt 61 is referred to as a so-called a parent and is configured like a band. The first belt 61 includes a first hole portion 61a provided at a first end portion of the first belt 61 and extending orthogonally to the longitudinal direction of the first belt 61, a second hole portion 61b provided at a second end portion of the first belt 61 and extending orthogonally to the longitudinal direction of the first belt 61, and a buckle 61c provided on the second hole portion 61b. The first hole portion 61a has an inner diameter at which the spring rod 31b can be inserted into the first hole portion 61a and at which the first belt 61 can rotate with respect to the spring rod 31b. In other words, the first belt 61 is rotatably held by the outer case 31 by disposing the first hole portion 61a between the pair of lugs 31a and around the spring rod 31b.

The second hole portion 61b is provided at a tip of the first belt 61. The buckle 61c includes a frame body 61d in a rectangular frame shape and a prong 61e rotatably attached to the frame body 61d. A side of the frame body 61d to which the prong 61e is attached is inserted into the second hole portion 61b, and the frame body 61d is attached to the first belt 61 rotatably with respect to the first belt 61.

The second belt 62 is referred to as a so-called blade tip, and is configured in a band-like shape having a width at which the second belt 62 can be inserted into the frame body 61*d*. In addition, the second belt 62 includes a plurality of small holes 62*a* into which the prong 61*e* is inserted. Additionally, the second belt 62 includes a third hole portion 62*b* provided at first end portion of the second belt 62 and extending orthogonally to the longitudinal direction of the second belt 62. The third hole portion 62*b* has an inner diameter at which the spring rod 31*b* can be inserted into the third hole portion 62*b* and at which the second belt 62 can rotate with respect to the spring rod 31*b*. In other words, the second belt 62 is rotatably held by the outer case 31 by disposing the third hole portion 62*b* between the pair of lugs 31*a* and around the spring rod 31*b*.

In the belt 4 as described above, the second belt 62 is inserted into the frame body 61*d* and the prong 61*e* is inserted into the small hole 62*a* to integrally connect the first belt 61 and the second belt 62, and the belt 4 comes to have an annular shape extending in such a manner as to follow along the circumferential direction of the wrist 200 along with the outer case 31.

The curler 5 is configured in a band-like shape that curves along the circumferential direction of the wrist. The curler 5 is formed with a first end and a second end spaced apart from each other. For example, a first end-side outer surface of the curler 5 is fixed to the back lid 35 of the device body 3. The first end and the second end of the curler 5 are disposed at positions where the first end and the second end protrude from the back lid 35. Furthermore, the first end and the second end of the curler 5 are located adjacent to each other at a predetermined distance from each other.

As a specific example, the curler 5 is fixed to a living body side end portion of the outer case 31 or the base 33 along with the back lid 35 using screws 35*a* or the like. Additionally, the curler 5 is fixed to the back lid 35 such that the first end and the second end are located on one lateral side of the wrist 200 when the blood pressure measurement device 1 is attached to the wrist 200.

As a specific example, as illustrated in FIG. 1, FIG. 2, and FIG. 4, the curler 5 has a shape that curves along a direction orthogonal to the circumferential direction of the wrist 200, in other words, along the circumferential direction of the wrist 200 in a side view from the longitudinal direction of the wrist 200. The curler 5 extends, for example, from the device body 3 through the hand back side of the wrist 200 and one lateral side of the wrist 200 to the hand palm side of the wrist 200 and toward the other lateral side of the wrist 200. Specifically, by curving along the circumferential direction of the wrist 200, the curler 5 is disposed across the most of the wrist 200 in the circumferential direction, with both ends of the curler 5 spaced at a predetermined distance from each other.

The curler 5 has hardness appropriate to provide flexibility and shape retainability. Here, "flexibility" refers to deformation of the shape of the curler 5 in a radial direction at the time of application of an external force of the belt 4 to the curler 5. For example, "flexibility" refers to deformation of the shape of the curler 5 in a side view in which the curler 5 approaches the wrist, is along the shape of the wrist, or follows to the shape of the wrist when the curler 5 is pressed by the belt 4. Furthermore, "shape retainability" refers to the ability of the curler 5 to maintain a pre-imparted shape when no external force is applied to the curler 5. For example, "shape retainability" refers to, in the present embodiment, the ability of the curler 5 to maintain the shape in a shape curving along the circumferential direction of the wrist.

The cuff structure 6 is disposed on an inner circumferential surface of the curler 5, and is held along the shape of the inner circumferential surface of the curler 5. As a specific example, the palm-side cuff 71 and the back-side cuff 74 are disposed on the inner circumferential surface of the curler 5 and the palm-side cuff 71 and the back-side cuff 74 are bonded using a bonding layer 8 such as an adhesive or a double-sided tape.

The curler 5 is formed of a resin material. The curler 5 is formed of, for example, polypropylene and has a thickness of approximately 1 mm.

As illustrated in FIGS. 1 to 4 and 7 to 13, the cuff structure 6 includes the palm-side cuff (cuff) 71, a back plate 72, the sensing cuff 73, and the back-side cuff (cuff) 74. The cuff structure 6 is fixed to the curler 5. The cuff structure 6 includes the palm-side cuff 71, the back plate 72, and the sensing cuff 73 that are stacked one another and disposed on the curler 5, and the back-side cuff 74 that is spaced apart from the palm-side cuff 71, the back plate 72, and the sensing cuff 73 and disposed on the curler 5.

As a specific example, the cuff structure 6 includes the palm-side cuff 71, the back plate 72, the sensing cuff 73, and the back-side cuff 74 that are disposed on an inner surface of the curler 5. The cuff structure 6 is fixed to the inner surface of the curler 5 on the hand palm side of the wrist 200 with the palm-side cuff 71, the back plate 72, and the sensing cuff 73 stacked in this order from the inner surface of the curler 5 toward the living body. In addition, the cuff structure 6 includes the back-side cuff 74 disposed on the inner surface of the curler 5 on the hand back side of the wrist 200. Each of the members of the cuff structure 6 is fixed to an adjacent member of the cuff structure 6 in a stacking direction with a double-sided tape, an adhesive, or the like.

The palm-side cuff 71 is a so-called pressing cuff. The palm-side cuff 71 is fluidly connected to the pump 14 through the flow path unit 15. The palm-side cuff 71 is inflated to press the back plate 72 and the sensing cuff 73 toward the living body side. The palm-side cuff 71 includes a plurality of, for example, two-layer air bags 81 and a bonded portion 82 disposed on the curler 5 side of the air bags 81.

Here, the air bags 81 are bag-like structures, and in the present embodiment, the blood pressure measurement device 1 is configured to use air with the pump 14, and thus the present embodiment will be described using the air bags. However, in a case where a fluid other than air is used, the bag-like structures may be fluid bags such as liquid bags. The plurality of air bags 81 are stacked and are in fluid communication with one another in the stacking direction.

Each of the two-layer air bags 81 is constituted in a rectangular shape that is long in one direction. The air bag 81 is constituted, for example, by combining two sheet members 86 that are long in one direction, and thermally welding edges of the sheet members. As a specific example, as illustrated in FIGS. 7 to 9, the two-layer air bags 81 include a first sheet member 86*a*, a second sheet member 86*b*, a third sheet member 86*c*, and a fourth sheet member 86*d* in this order from the living body side. The second sheet member 86*b* constitutes a first-layer air bag 81 along with the first sheet member 86*a*, the third sheet member 86*c* is integrally bonded to the second sheet member 86*b*, and the fourth sheet member 86*d* constitutes a second-layer air bag 81 along with the third sheet member 86*c*. Note that the two-layer air bags 81 are integrally constituted by joining each of the sheet members 86 of the adjacent air bags 81 by bonding with a double-sided tape, an adhesive, or the like, or welding or the like.

Edge portions of four sides of the first sheet member 86*a* are welded to corresponding edge portions of four sides of the second sheet member 86b to constitute the air bag 81. The second sheet member 86b and the third sheet member 86c are disposed facing each other, and each includes a plurality of openings 86b1 and 86c1 through which the two air bags 81 are fluidly continuous.

Edge portions of four sides of the third sheet member 86c are welded to corresponding edge portions of four sides of the fourth sheet member 86d to constitute the air bag 81. The fourth sheet member 86d is disposed on the curler 5 side and is joined to the inner circumferential surface of the curler 5 with the bonded portion 82 in between.

The bonded portion 82 is integrally provided on the fourth sheet member 86d disposed on the curler 5 side of the two-layer air bags 81. As illustrated in FIGS. 9 and 12, the bonded portion 82 is bonded to the curler 5 with the bonding layer 8 such as an adhesive or double-sided tape in between. For example, the entire main surface or substantially the entire main surface of the bonded portion 82 facing the curler 5 is bonded to the curler 5. Here, an example of a case in which substantially the entire surface of the bonded portion 82 and the curler 5 are bonded includes a case of bonding with a plurality of double-sided tapes leading to formation of gaps or the like between the double-sided tapes in a surface direction, when the bonding layer 8 is constituted by a double-sided tape.

The bonded portion 82 is integrally welded to the fourth sheet member 86d. As a specific example, the bonded portion 82 is a sheet member 86 formed like a rectangle that is substantially the same as the shape of the fourth sheet member 86d.

Like welded portions 150 illustrated in FIG. 12, the bonded portion 82 is welded at a position closer to the center of the fourth sheet member 86d than edge portions corresponding to the welded portions of the third sheet member 86c and the fourth sheet member 86d that constitute the air bag 81 on the curler 5 side.

The back plate 72 is applied to an outer surface of the first sheet member 86a of the palm-side cuff 71 with an adhesive layer, a double-sided tape, or the like. The back plate 72 is formed in a plate shape using a resin material. The back plate 72 is made of polypropylene, for example, and is formed into a plate shape having a thickness of approximately 1 mm. The back plate 72 has shape followability.

Here, "shape followability" refers to a function of the backplate 72 by which the back plate 72 can be deformed in such a manner as to follow the shape of a contacted portion of the wrist 200 to be disposed, the contacted portion of the wrist 200 refers to a region of the wrist 200 that is faced by the back plate 72, and the contact as used herein includes both direct contact and indirect contact with the sensing cuff 73 in between.

For example, as illustrated in FIG. 9, the back plate 72 includes a plurality of grooves 72a formed in both main surfaces of the back plate 72 and extending in a direction orthogonal to the longitudinal direction. As illustrated in FIG. 9, a plurality of the grooves 72a are provided in both main surfaces of the back plate 72. The plurality of grooves 72a provided in one of the main surfaces face the corresponding grooves 72a provided in the other main surface in the thickness direction of the back plate 72. Additionally, the plurality of grooves 72a are disposed at equal intervals in the longitudinal direction of the back plate 72.

In the back plate 72, portions including the plurality of grooves 72a are thinner than portions including no grooves 72a and thus the portions including the plurality of grooves 72a are easily deformed. Thus, the back plate 72 is deformed in such a manner as to follow along the shape of the wrist 200 and has shape followability of extending in the circumferential direction of the wrist 200. The back plate 72 is formed such that the length of the back plate 72 is sufficient to cover the hand palm side of the wrist 200. The back plate 72 transfers the pressing force from the palm-side cuff 71 to the back plate 72 side main surface of the sensing cuff 73 in a state in which the back plate 72 is extending along the shape of the wrist 200.

The sensing cuff 73 is fixed to the living body side main surface of the back plate 72. The sensing cuff 73 is in direct contact with a region of the wrist 200 where an artery 210 resides, as illustrated in FIG. 9. The artery 210 as used herein is the radial artery and the ulnar artery. The sensing cuff 73 is formed in the same shape as that of the back plate 72 or a shape that is smaller than that of the back plate 72, in the longitudinal direction and the width direction of the back plate 72. The sensing cuff 73 is inflated to compress a hand palm-side region of the wrist 200 in which the artery 210 resides. The sensing cuff 73 is pressed by the inflated palm-side cuff 71 toward the living body side with the back plate 72 in between.

As a specific example, the sensing cuff 73 includes one air bag 91, a tube 92 that communicates with the air bag 91, and a connection portion 93 provided at a tip of the tube 92. One main surface of the air bag 91 of the sensing cuff 73 is fixed to the back plate 72. For example, the sensing cuff 73 is applied to the living body side main surface of the back plate 72 using a double-sided tape, an adhesive layer, or the like.

Here, the air bag 91 is a bag-like structure, and in the present embodiment, the blood pressure measurement device 1 is configured to use air with the pump 14, and thus the present embodiment will be described using the air bag. However, in a case where a fluid other than air is used, the bag-like structure may be a liquid bag and the like.

The air bag 91 is constituted in a rectangular shape that is long in one direction. The air bag 91 is constituted, for example, by combining two sheet members that are long in one direction, and thermally welding edges of the sheet members. As a specific example, the air bag 91 includes a fifth sheet member 96a and a sixth sheet member 96b in this order from the living body side as illustrated in FIGS. 9 and 12.

For example, the fifth sheet member 96a and the sixth sheet member 96b are fixed by welding, with a tube 92 that is fluidly continuous with the internal space of the air bag 91 being disposed on one side of each of the fifth sheet member 96a and the sixth sheet member 96b. For example, the fifth sheet member 96a and the sixth sheet member 96b are welded together integrally with the tube 92 by welding edge portions of four sides of the fifth sheet member 96a to corresponding edge portions of four sides of the sixth sheet member 96b in a state in which the tube 92 is disposed between the fifth sheet member 96a and the sixth sheet member 96b.

The tube 92 is provided at one longitudinal end portion of the air bag 91. As a specific example, the tube 92 is provided at an end portion of the air bag 91 near the device body 3. The tube 92 includes the connection portion 93 at the tip. The tube 92 is connected to the flow path unit 15 and constitutes a flow path between the device body 3 and the air bag 91. The connection portion 93 is connected to the flow path unit 15. The connection portion 93 is, for example, a nipple.

The back-side cuff 74 is a so-called tensile cuff. The back-side cuff 74 is fluidly connected to the pump 14 through the flow path unit 15. The back-side cuff 74 is inflated to press the curler 5 such that the curler 5 is spaced apart from the wrist 200, pulling the belt 4 and the curler 5 toward the hand back side of the wrist 200. The back-side cuff 74 includes air bags 101 including a plurality of, for example, six layers, a tube 102 in communication with the air bags 101, a connection portion 103 provided at a tip of the tube 102, and a bonded portion 104 disposed on the curler 5 side of the air bag 101.

Additionally, the back-side cuff 74 is configured such that the thickness of the back-side cuff 74 in an inflating direction, in the present embodiment, in the direction in which the curler 5 and the wrist 200 face each other, during inflation, is larger than the thickness of the palm-side cuff 71 in the inflating direction during inflation and than the thickness of the sensing cuff 73 in the inflating direction during inflation. Specifically, the air bags 101 of the back-side cuff 74 include more layers than the air bags 81 in the palm-side cuff 71 and the air bag 91 in the sensing cuff 73, and are thicker than the palm-side cuff 71 and the sensing cuff 73 when the air bags 101 are inflated from the curler 5 toward the wrist 200.

Here, the air bag 101 is a bag-like structure, and in the present embodiment, the blood pressure measurement device 1 is configured to use air with the pump 14, and thus the present embodiment will be described using the air bag. However, in a case where a fluid other than air is used, the bag-like structure may be a fluid bag such as a liquid bag. A plurality of the air bags 101 are stacked and are in fluid communication in the stacking direction.

The six-layer air bags 101 are constituted in a rectangular shape that is long in one direction. The air bag 101 is constituted, for example, by combining two sheet members 106 that are long in one direction, and thermally welding edges of the sheet members. As a specific example, as illustrated in FIGS. 10 and 13, the six-layer air bags 101 include a seventh sheet member 106a, an eighth sheet member 106b, a ninth sheet member 106c, a tenth sheet member 106d, an eleventh sheet member 106e, a twelfth sheet member 106f, a thirteenth sheet member 106g, a fourteenth sheet member 106h, a fifteenth sheet member 106i, a sixteenth sheet member 106j, a seventeenth sheet member 106k, and an eighteenth sheet member 106l in this order from the living body side. Note that the six-layer air bags 101 are integrally constituted by joining each of the sheet members 106 of the adjacent air bags 101 by bonding with a double-sided tape, an adhesive, or the like, or welding or the like.

Edge portions of four sides of the seventh sheet member 106a are welded to corresponding edge portions of four sides of the eighth sheet member 106b to constitute a first-layer air bag 101. The eighth sheet member 106b and the ninth sheet member 106c are disposed facing each other and are integrally bonded together. The eighth sheet member 106b and the ninth sheet member 106c include a plurality of openings 106b1 and 106c1 through which the adjacent air bags 101 are fluidly continuous. Edge portions of four sides of the ninth sheet member 106c are welded to corresponding edge portions of four sides of the tenth sheet member 106d to constitute a second-layer air bag 101.

The tenth sheet member 106d and the eleventh sheet member 106e are disposed facing each other and are integrally bonded together. The tenth sheet member 106d and the eleventh sheet member 106e include a plurality of openings 106d1 and 106e1 through which the adjacent air bags 101 are fluidly continuous. Edge portions of four sides of the eleventh sheet member 106e are welded to corresponding edge portions of four sides of the twelfth sheet member 106f to constitute a third-layer air bag 101.

The twelfth sheet member 106f and the thirteenth sheet member 106g are disposed facing each other and are integrally bonded together. The twelfth sheet member 106f and the thirteenth sheet member 106g include a plurality of openings 106f1 and 106g1 through which the adjacent air bags 101 are fluidly continuous. Edge portions of four sides of the thirteenth sheet member 106g are welded to corresponding edge portions of four sides of the fourteenth sheet member 106h to constitute a fourth-layer air bag 101.

The fourteenth sheet member 106h and the fifteenth sheet member 106i are disposed facing each other and are integrally bonded together. The fourteenth sheet member 106h and the fifteenth sheet member 106i include a plurality of openings 106h1 and 106i1 through which the adjacent air bags 101 are fluidly continuous. Edge portions of four sides of the fifteenth sheet member 106i are welded to corresponding edge portions of four sides of the sixteenth sheet member 106j to constitute a fifth-layer air bag 101.

The sixteenth sheet member 106j and the seventeenth sheet member 106k are disposed facing each other and are integrally bonded together. The sixteenth sheet member 106j and the seventeenth sheet member 106k include a plurality of openings 106j1 and 106k1 through which the adjacent air bags 101 are fluidly continuous. Edge portions of four sides of the seventeenth sheet member 106k are welded to corresponding edge portions of four sides of the eighteenth sheet member 106l to constitute a sixth-layer air bag 101. The eighteenth sheet member 106l is disposed on the curler 5 side and is joined to the inner circumferential surface of the curler 5 with the bonded portion 82 in between.

In addition, for example, a tube 102 that is fluidly continuous with the internal space of the air bag 101 is disposed on one side of the seventeenth sheet member 106k and the eighteenth sheet member 106l, and is fixed by welding. For example, in a state in which the tube 102 is disposed between the seventeenth sheet member 106k and the eighteenth sheet member 106l, the edge portions of the seventeenth sheet member 106k are welded to the edge portions of the eighteenth sheet member 106l in a rectangular frame shape to form the air bag 101. Thus, the tube 102 is integrally welded to the air bag 101.

For example, the sixth-layer air bag 101 as described above is constituted integrally with the second layer air bag 81 of the palm-side cuff 71. Specifically, the seventeenth sheet member 106k is constituted integrally with the third sheet member 86c, and the eighteenth sheet member 106l is constituted integrally with the fourth sheet member 86d.

In more detail, the third sheet member 86c and the seventeenth sheet member 106k constitute a rectangular sheet member that is long in one direction, and the eighteenth sheet member 106l and the fourth sheet member 86d constitute a rectangular sheet member that is long in one direction. Then, the sheet members are stacked on each other, and first end portions are welded together in a rectangular frame shape, whereas second end portions are welded together except for a part of one side of each end portion, to constitute the second-layer air bag 81 in the palm-side cuff 71, and then the second end portions are welded together in a rectangular frame shape, whereas the first end portions are welded together except for a part of one side of each end portion, to constitute the sixth-layer air bag 81 in the back-side cuff 74. In addition, a part of one side on the facing side of each of the second-layer air bag 81 and the sixth-layer air bag 101 is not welded, and thus the second-layer air bag 81 and the sixth-layer air bag 101 are fluidly continuous.

The tube 102 is connected to one air bag 101 of the six-layer air bags 101 and is provided at one longitudinal end portion of the air bag 101. As a specific example, the tube 102 is provided on the curler 5 side of the six-layer air bags 101 and is provided at the end portion close to the device body 3. The tube 102 includes a connection portion 103 at the tip. The tube 102 constitutes a flow path included in the fluid circuit 7 and located between the device body 3 and the air bags 101. The connection portion 103 is, for example, a nipple.

Note that, as described above, in the present embodiment, the configuration has been described in which a part of the back-side cuff 74 is constituted integrally with the palm-side cuff 71 and is fluidly continuous with the palm-side cuff 71. However, no such limitation is intended. For example, as illustrated in FIG. 8, the back-side cuff 74 may be constituted separately from the palm-cuff 71 and may be fluidly discontinuous with the palm-side cuff 71. For such a configuration, the back-side cuff 74 may be configured such that, like the sensing cuff 73 and the palm-side cuff 71, the back-side cuff 74 is further provided with a tube and a connection portion, and in the fluid circuit 7 as well, the back-side cuff 74 is connected to a flow path through which the fluid is fed to the back-side cuff 74, a check valve, and a pressure sensor.

The bonded portion 104 is integrally provided on the eighteenth sheet member 106*l* disposed on the curler 5 side of the two-layer air bags 81. As illustrated in FIGS. 10 and 13, the bonded portion 104 is bonded to the curler 5 with the bonding layer 8 such as an adhesive or a double-sided tape in between. For example, the bonded portion 104 is bonded to the entire main surface or substantially the entire main surface facing the curler 5. Here, an example of a case in which substantially the entire surface of the bonded portion 104 and the curler 5 are bonded includes a case of bonding with a plurality of double-sided tapes leading to formation of gaps or the like between the double-sided tapes in the surface direction, when the bonding layer 8 is constituted by a double-sided tape.

Note that in a case of configuration in which a part of the back-side cuff 74 is integrally constituted with the palm-side cuff 71 and is fluidly continuous with the palm-side cuff 71, the bonded portion 82 and the bonded portion 104 may be configured to be integrally continuous, or may be configured to be provided at positions corresponding to the palm-side cuff 71 and the back-side cuff 74, respectively. In the present embodiment, a configuration will be described in which the bonded portion 82 and the bonded portion 104 are provided separately from each other.

The bonded portion 104 is integrally welded to the eighteenth sheet member 106*l*. As a specific example, the bonded portion 104 is the sheet member 106 formed like a rectangle substantially the same as the shape of the eighteenth sheet member 106*l*. Like the welded portions 150 illustrated in FIG. 13, the bonded portion 104 is welded at a position closer to the center of the eighteenth sheet member 106*l* than edge portions corresponding to the welded portions of the seventeenth sheet member 106*k* and the eighteenth sheet member 106*l* that constitute the air bag 101 on the curler 5 side.

Additionally, each of the sheet members 86, 96, and 106 forming the palm-side cuff 71, the sensing cuff 73, and the back-side cuff 74 are formed of a thermoplastic resin material. The thermoplastic resin material is a thermoplastic elastomer. Examples of thermoplastic resin material constituting the sheet members 86, 96, and 106 include thermoplastic polyurethane based resin (hereinafter referred to as TPU), polyvinyl chloride resin, ethylene-vinyl acetate resin, thermoplastic polystyrene based resin, thermoplastic polyolefin resin, thermoplastic polyester based resin, and thermoplastic polyamide resin.

For example, the sheet members 86, 96, and 106 are formed using a molding method such as T-die extrusion molding or injection molding. After being molded by each molding method, the sheet members 86, 96, and 106 are sized into predetermined shapes, and the sized individual pieces are joined by welding or the like to constitute bag-like structures 81, 91, and 101. A high frequency welder or laser welding is used as the welding method.

The fluid circuit 7 is constituted by the case 11, the pump 14, the flow path unit 15, the on-off valves 16, the pressure sensors 17, the palm-side cuff 71, the sensing cuff 73, and the back-side cuff 74. A specific example of the fluid circuit 7 will be described below with two on-off valves 16 that are used in the fluid circuit 7 being designated as a first on-off valve 16A and a second on-off valve 16B, and two pressure sensors 17 that are used in the fluid circuit 17 being designated as a first pressure sensor 17A and a second pressure sensor 17B.

As illustrated in FIG. 5, the fluid circuit 7 includes, for example, a first flow path 7*a* that makes the palm-side cuff 71 and the back-side cuff 74 continuous with the pump 14, a second flow path 7*b* constituted by branching from a middle portion of the first flow path 7*a* and making the sensing cuff 73 continuous with the pump 14, and a third flow path 7*c* connecting the first flow path 7*a* to the atmosphere. Additionally, the first flow path 7*a* includes the first pressure sensor 17A. The first on-off valve 16A is provided between the first flow path 7*a* and the second flow path 7*b*. The second flow path 7*b* includes a second pressure sensor 17B. The second on-off valve 16B is provided between the first flow path 7*a* and the third flow path 7*c*.

In the fluid circuit 7 as described above, the first on-off valve 16A and the second on-off valve 16B are closed to connect only the first flow path 7*a* to the pump 14, and the pump 14 and the palm-side cuff 71 are fluidly connected. In the fluid circuit 7, the first on-off valve 16A is opened and the second on-off valve 16B is closed to connect the first flow path 7*a* and the second flow path 7*b*, thus fluidly connecting the pump 14 and the back-side cuff 74, the back-side cuff 74 and the palm-side cuff 71, and the pump 14 and the sensing cuff 73. In the fluid circuit 7, the first on-off valve 16A is closed and the second on-off valve 16B is opened to connect the first flow path 7*a* and the third flow path 7*c*, fluidly connecting the palm-side cuff 71, the back-side cuff 74, and the atmosphere together. In the fluid circuit 7, the first on-off valve 16A and the second on-off valve 16B are opened to connect the first flow path 7*a*, the second flow path 7*b*, and the third flow path 7*c*, fluidly connecting the palm-side cuff 71, the sensing cuff 73, the back-side cuff 74, and the atmosphere together.

Now, an example of measurement of a blood pressure value using the blood pressure measurement device 1 will be described using FIGS. 14 to 17. FIG. 14 is a flowchart illustrating an example of a blood pressure measurement using the blood pressure measurement device 1, illustrating both an operation of a user and an operation of the control unit 55. Additionally, FIGS. 15 to 17 illustrate an example of the user wearing the blood pressure measurement device 1 on the wrist 200.

First, the user attaches the blood pressure measurement device 1 to the wrist 200 (step ST1). As a specific example, for example, the user inserts one of the wrists 200 into the curler 5, as illustrated in FIG. 15.

At this time, in the blood pressure measurement device 1, the device body 3 and the sensing cuff 73 are disposed at opposite positions in the curler 5, and thus the sensing cuff 73 is disposed in a region on the hand palm side of the wrist 200 in which the artery 210 resides. Thus, the device body 3 and the back-side cuff 74 are disposed on the hand back side of the wrist 200. Then, as illustrated in FIG. 16, the user passes the second belt 62 through the frame body 61*d* of the buckle 61*c* of the first belt 61 with the hand opposite to the hand on which the blood pressure measurement device 1 is disposed. The user then pulls the second belt 62 to bring the member on the inner circumferential surface side of the curler 5, that is, the cuff structure 6, into close contact with the wrist 200, and inserts the prong 61*e* into the small hole 62*a*. Thus, as illustrated in FIG. 17, the first belt 61 and the second belt 62 are connected, and the blood pressure measurement device 1 is attached to the wrist 200.

Then, the user operates the operation unit 13 to input an instruction corresponding to the start of measurement of the blood pressure value. The operation unit 13, on which an input operation of the instruction has been performed, outputs an electrical signal corresponding to the start of the measurement to the control unit 55 (step ST2). The control unit 55 receives the electrical signal, and then for example, opens the first on-off valve 16A, closes the second on-off valve 16B, and drives the pump 14 to feed compressed air to the palm-side cuff 71, the sensing cuff 73, and the back-side cuff 74 through the first flow path 7*a* and the second flow path 7*b* (step ST3). Thus, the palm-side cuff 71, the sensing cuff 73, and the back-side cuff 74 start to be inflated.

The first pressure sensor 17A and the second pressure sensor 17B detect the pressures in the palm-side cuff 71, the sensing cuff 73, and the back-side cuff 74, and outputs, to the control unit 55, electrical signals corresponding to the pressures (step ST4). Based on the received electrical signals, the control unit 55 determines whether the pressures in the internal spaces of the palm-side cuff 71, the sensing cuff 73, and the back-side cuff 74 have reached a predetermined pressure for measurement of the blood pressure (step ST5). For example, in a case where the internal pressures of the palm-side cuff 71 and the back-side cuff 74 have not reached the predetermined pressure and the internal pressure of the sensing cuff 73 has reached the predetermined pressure, the control unit 55 closes the first on-off valve 16A and feeds compressed air through the first flow path 7*a*.

When the internal pressures of the palm-side cuff 71 and the back-side cuff 74 and the internal pressure of the sensing cuff 73 all have reached the predetermined pressure, the control unit 55 stops driving the pump 14 (YES in step ST5). At this time, as illustrated in FIGS. 11 to 13, the palm-side cuff 71 and the back-side cuff 74 are sufficiently inflated, and the inflated palm-side cuff 71 presses the back plate 72. Additionally, the back-side cuff 74 presses against the curler 5 in a direction away from the wrist 200, and then the belt 4, the curler 5, and the device body 3 move in a direction away from the wrist 200, and as a result, the palm-side cuff 71, the back plate 72, and the sensing cuff 73 are pulled toward the wrist 200 side. In addition, when the belt 4, the curler 5, and the device body 3 move in a direction away from the wrist 200 due to the inflation of the back-side cuff 74, the belt 4 and the curler 5 move toward both lateral sides of the wrist 200, and the belt 4, the curler 5, and the device body 3 move in a state of close contact with both lateral sides of the wrist 200. Thus, the belt 4 and the curler 5, which are in close contact with the skin of the wrist 200, pull the skin on both lateral sides of the wrist 200 toward the hand back side. Note that the curler 5 may be configured to indirectly contact the skin of the wrist 200 with the sheet members 86 or 106 in between, for example, as long as the curler 5 can pull the skin of the wrist 200.

Further, the sensing cuff 73 is inflated by being fed with a predetermined amount of air such that the internal pressure equals the pressure required to measure blood pressure, and is pressed toward the wrist 200 by the back plate 72 that is pressed by the palm-side cuff 71. Thus, the sensing cuff 73 presses the artery 210 in the wrist 200 and occludes the artery 210 as illustrated in FIG. 12.

Additionally, the control unit 55, for example, controls the second on-off valve 16B and repeats the opening and closing of the second on-off valve 16B, or adjusts the degree of opening of the second on-off valve 16B to pressurize the internal space of the palm-side cuff 71. In the process of pressurization, based on the electrical signal output by the second pressure sensor 17B, the control unit 55 obtains measurement results such as blood pressure values, for example, the systolic blood pressure and the diastolic blood pressure, and the heart rate and the like (step ST6). The control unit 55 outputs an image signal corresponding to the obtained measurement results to the display unit 12, and displays the measurement results on the display unit 12 (step ST7). In addition, after the end of the blood pressure measurement, the control unit 55 opens the first on-off valve 16A and the second on-off valve 16B.

The display unit 12 receives the image signal, and then displays the measurement results on the screen. The user views the display unit 12 to confirm the measurement results. After the measurement is complete, the user removes the prong 61*e* from the small hole 62*a*, removes the second belt 62 from the frame body 61 *d*, and removes the wrist 200 from the curler 5, thus removing the blood pressure measurement device 1 from the wrist 200.

The blood pressure measurement device 1 according to one embodiment configured in this manner has a configuration in which the palm-side cuff 71 and the back-side cuff 74, serving as the cuff, are provided with the bonded portions 82 and 104 bonded to the curler 5 with the bonding layer 8 in between. The bonded portions 82 and 104 are welded to the adjacent sheet members 86 and 106 at a position closer to the center of the sheet members 86 and 106 than the edge portions corresponding to the welded portions of the two sheet members 86 and 106 that constitute the air bags 81 and 101 adjacent to the curler 5 of the palm-side cuff 71 and the back-side cuff 74. In other words, as illustrated in FIG. 12 and FIG. 13, the bonded portions 82 and 104, and the sheet members 86*d* and 106*l* include the welded portions 150 at positions closer to the center than the welded portion for forming the adjacent sheet members 86 and 106 into the air bags 81 and 101.

Thus, in the blood pressure measurement device 1, when the air bags 81 and 101 are inflated, the stress occurred in the bonded portions 82 and 104 by inflation of the air bags 81 and 101 occurs at a position closer to the center of the bonded portions 82 and 104 than the outer peripheral edges of the bonded portions 82 and 104. Thus, when the air bags 81 and 101 are inflated, the stress applied to the bonding layer 8 applies in a tensile direction from the bonding surface of the bonded portions 82 and 104. This enables a reduction in stress applied between the curler 5 and the cuff structure 6 when the air bags 81 and 101 are inflated, and thus even in a case where the adhesive, double-sided tape, or the like used as the bonding layer 8 provides he same junction strength as that of the adhesive, double-sided tape, and the like used in the related art, peel-off of the palm-side cuff 71 and the back-side cuff 74 from the curler 5 can be suppressed.

This effect will be described in detail using FIG. 12, FIG. 13, and FIG. 18. FIG. 18 is an explanatory diagram illustrating an example of the direction of stress occurring in the bonded portions 82 and 104 of the cuffs 71 and 74 of the present embodiment and the direction of stress occurring in the sheet members 86 and 106 of the cuff in a conventional example. Note that the blood pressure measurement device in (CONVENTIONAL EXAMPLE) in FIG. 18 does not include the bonded portion 82 or 104.

First, the air bags 81 and 101 bulge more significantly on the center side of the air bags 81 and 101 than on the end portion side of the air bags 81 and 101.

In a case of the blood pressure measurement device in the conventional example where the fourth sheet member 86d and the eighteenth sheet member 106l are bonded directly to the curler 5 without including the bonded portion 82, the center side of the air bags 81 and 101 remain bonded to the curler 5, whereas the end portion side of the air bags 81 and 101 are subjected to a force acting in the direction in which the air bags 81 and 101 are separated from the curler 5.

As a result, in a configuration without including the bonded portion 82, the stress applied to the bonding layer 8 bonding the air bags 81 and 101 to the curler concentrates on the edge sides of the air bags 81 and 101. Then, in (CONVENTIONAL EXAMPLE) in FIG. 18 where stress is indicated by an arrow, the stress occurs in the bonding layer 8 to peel off the sheet members 86 and 106 from the curler 5 such that the peel-off originates from the edge side of the air bags 81 and 101. Thus, repeated inflation and contraction of the air bags 81 and 101 may cause the air bags 81 and 101 to peel off from the curler 5. This occurs particularly when the width for bonding is reduced, and thus the air bags 81 and 101 may peel off from the curler 5 such that the peel-off originates from the widthwise edges of the air bags 81 and 101 in a direction orthogonal to the longitudinal direction of the air bags 81 and 101.

However, in the blood pressure measurement device 1 of the present embodiment, the welded portions 150 where the bonded portions 82 and 104 and the air bags 81 and 101 are welded together are located at positions closer to the center of the air bags 81 and 101 than the welded portions at the edge portions of the air bags 81 and 101. In addition, the bonded portions 82 and 104 and the air bags 81 and 101 are continuous at the welded portions 150.

Thus, first, the air bags 81 and 101 bulge more significantly in the areas where the welded portions 150 are provided than at the end portions of the air bags 81 and 101. Thus, the force in a direction away from the curler 5 is weaker in the areas where the welded portions 150 are provided than at the end portions of the air bags 81 and 101.

Next, the force occurred in the bonded portions 82 and 104 by inflation of the air bags 81 and 101 and acting in the direction away from the curler 5 corresponds to a force in a direction orthogonal to or approximately orthogonal to the surface direction of the bonded portions 82 and 104 and the curler 5. Thus, the stress occurring in the bonding layer 8 facing the welded portions 150 and acting in the direction in which the curler 5 and the bonded portions 82 and 104 are separated from each other corresponds to tensile stress corresponding to the stress indicated by an arrow in (EMBODIMENT) in FIG. 18. Furthermore, the tensile stress is less likely to separate the air bags 81 and 101 (bonded portions 82 and 104) from the curler 5 than the peeling stress.

Furthermore, the entire surface of the bonded portions 82 and 104 are bonded to the curler 5, and thus a bonding area can be secured. Thus, bonding the air bags 81 and 101 to the curler 5 with the bonded portions 82 and 104 in between allows peel-off of the cuffs 71 and 74 from the curler 5 to be suppressed more properly than the conventional example not including the bonded portions 82 and 104 and in which the air bags 81 and 101 are bonded directly to the curler 5.

As described above, the blood pressure measurement device 1 provided with the bonded portions 82 and 104 can suppress peel-off of the air bags 81 and 101 from the curler 5, the peel-off originating from the edge portion side. In this way, even with the use of the same bonding layer 8 as that in the related art, the blood pressure measurement device 1 provided with the bonded portions 82 and 104 can suppress the peeling between the curler 5 and the cuff structure 6.

As a result, the blood pressure measurement device 1 can have high durability against repeated inflation and contraction of the cuff structure 6, and can perform blood pressure measurements with high accuracy for extended periods of time.

In addition, the blood pressure measurement device 1 can suppress the peeling between the curler 5 and the cuff structure 6, the width of the air bags 81 and 101 in the direction orthogonal to the longitudinal direction of the air bags 81 and 101 can be reduced. Thus, the blood pressure measurement device 1 can be miniaturized.

In addition, the blood pressure measurement device 1 has a configuration in which the position of the stress concentration point, when the palm-side cuff 71 and the back-side cuff 74 is inflated, is located to be on the center side of the bonding layer 8 by the bonded portions 82 and 104 and the welded portions 150. Thus, the blood pressure measurement device 1 can suppress deformation of the curler 5 due to repeated use.

This effect will be described using a specific example. For example, to make the cuff structure 6 less likely to peel off from the curler 5, a material that allows firm bonding may be used as the bonding layer 8 to bond, to the curler 5, a cuff structure with a known configuration not using the bonded portion 82 or 104. However, when a material having high bondability is used as the bonding layer 8, the curler 5 may deflect following inflation of the cuff structure 6 depending on the mechanical properties of the curler 5, When the inflation and contraction of the cuff structure 6 are repeated in a case in which the curler 5 deflects following the inflation of the cuff structure 6, creep deformation occurs in the curler 5, and the shape of the curler 5 is deflected, preventing suitable blood pressure measurement.

In contrast, the blood pressure measurement device 1 according to the present embodiment is configured such that instead of the curler 5, the stress concentration point is located on the center side of the bonding layer 8 by the bonded portions 82 and 104 to suppress an increase in the amount of deformation of the cuff structure 6, thus reducing the stress occurring at the junction portion between the curler 5 and the cuff structure 6. Thus, as described above, the blood pressure measurement device 1 can suppress deformation of the curler 5, allowing suppression of a decrease in the accuracy of the blood pressure measurement due to deformation of the curler 5.

As a result, the blood pressure measurement device 1 can be miniaturized, and highly accurate blood pressure measurement can be stably performed for a long period of time.

In addition, the bonded portions 82 and 104 are the sheet member 86 integrally welded to the sheet members 86d and 106l disposed on the curler 5 side of the air bags 81 and 101.

Thus, the bonded portions 82 and 104 and the sheet members 86d and 106l can be welded in the same step in which the two sheet members 86 and 106 constituting the air bags 81 and 101 are welded. This facilitates manufacturing and allows the same apparatus to be used. Additionally, the second members 82a and 104a and the sheet members 86d and 106l is constituted by the same resin material, allowing easy and suitable welding of the second members 82a and 104a and the sheet members 86d and 106l. Thus, the blood pressure measurement device 1 can reduce manufacturing costs and can be easily manufactured. In addition, the dimension of the cuff structure 6 in the thickness direction is increased only by an amount corresponding to the dimension of one sheet member 86 in the thickness direction, allowing suppression of an increase in the size of the blood pressure measurement device 1.

As described above, the blood pressure measurement device 1 according to the present embodiment enables the peeling between the curler 5 and cuff structure 6 to be suppressed.

Note that the present invention is not limited to the embodiments described above. In the example described above, the configuration has been described in which the bonded portions 82 and 104 are one sheet member 86 and is welded at a position closer to the center side than the welded portions of the welded sheet members 86 that constitute the adjacent air bags 81 and 101. However, no such limitation is intended.

For example, the present invention may include a configuration illustrated in a bonded portions 82A and 104A of a blood pressure measurement device 1A according to a second embodiment illustrated in FIG. 19. Hereinafter, a configuration of the bonded portions 82A and 104A will be described using FIG. 19. Note that the blood pressure measurement device 1A according to the second embodiment has a configuration similar to the configuration of the blood pressure measurement device 1 according to the first embodiment described above except the bonded portions 82A and 104A, and thus similar components are denoted by the same reference signs, and detailed descriptions of these components are omitted.

The bonded portions 82A and 104A are constituted by welding two sheet members 86 having the same shape as that of the sheet members 86 constituting the air bags 81 and 101 such that the two sheet members 86 for the bonded portions 82A and 104A are welded together over a width larger than the width over which the two sheet members 86 constituting the air bags 81 and 101 are welded together. In other words, the bonded portions 82A and 104A have a configuration in which the width of the junction margin corresponding to the welded portion of the air bags 81 and 101 are increased.

In other words, the bonded portions 82A and 104A have a bag-like structure formed like a bag configured to be inflated into a shape smaller than the air bags 81 and 101 when the bonded portions 82A and 104A are fed with a fluid. The bonded portions 82A and 104 as described above are welded to the sheet members 86d and 106l of the air bags 81 and 101 that face the curler 5, and are fluidly connected to the air bags 81 and 101 in a stacking direction.

The blood pressure measurement device 1A including the bonded portions 82A and 104A according to the second embodiment produce effects similar to the effects of the blood pressure measurement device 1 according to the first embodiment described above. In addition, the blood pressure measurement device 1A has a simple configuration in which the bonded portions 82A and 104A are formed, by welding the two sheet members 86 together, as a bag-like structure configured to be inflated to a shape smaller than the air bags 81 and 101. In other words, the bonded portions 82A and 104A have a simple configuration in which one layer of bag-like structure including an enlarged junction margin of the air bags 81 and 101 is added. Thus, the blood pressure measurement device 1A is substantially the same as addition of one layer of a plurality of air bags 81 and 101, and allows the bonded portions 82A and 104A to be manufactured inexpensively and easily. In addition, the dimension of the cuff structure 6 in the thickness direction is increased only by an amount corresponding to the dimension of the two sheet members 86 in the thickness direction, allowing suppression of an increase in the size of the blood pressure measurement device 1A.

Additionally, for example, the present invention may have a configuration illustrated in a bonded portions 82B and 104B of a blood pressure measurement device 1B according to a third embodiment illustrated in FIG. 20. Hereinafter, a configuration of the bonded portions 82B and 104B will be described using FIG. 20. Note that the blood pressure measurement device 1B according to the third embodiment has a configuration similar to the configuration of the blood pressure measurement device 1 according to the first embodiment and the blood pressure measurement device 1A according to the second embodiment described above except the bonded portions 82B and 104B, and thus similar components are denoted by the same reference signs, and detailed descriptions of these components are omitted.

The bonded portions 82B and 104B include the first bonded portions 82A and 104A and the second bonded portions 82 and 104. In other words, the bonded portions 82B and 104B include the bonded portions 82 and 104 of the first embodiment and the bonded portions 82A and 104A of the second embodiment described above, and the first bonded portions 82A and 104A and the second bonded portions 82 and 104 are welded to and stacked on the sheet members 86d and 106l of the air bags 81 and 101 that face the curler 5, in this order.

The blood pressure measurement device 1B including the bonded portions 82B and 104B according to the third embodiment produce effects similar to the effects of the blood pressure measurement device 1 according to the first embodiment and the blood pressure measurement device 1A according to the second embodiment. In addition, the dimension of the cuff structure 6 in the thickness direction is increased only by an amount corresponding to the dimension of three sheet members 86 in the thickness direction, allowing suppression of an increase in the size of the blood pressure measurement device 1B.

For example, in the example described above, the example in which the bonded portions 82 and 104 are constituted by the sheet members 86 has been described, but no such limitation is intended. For example, the bonded portions 82 and 104 may be constituted by a material similar to the material of the sheet member 86, the material having substantially the same shape as that of the sheet member 86 and having a higher bending strength than the sheet member 86. Furthermore, "similar materials" refer to two materials that are highly compatible with each other in thermal welding and that have the same softening temperature or close softening temperatures. "Compatibility" refers to the degree of mixing of the resin materials softened or melted during welding, and "high compatibility" means that junction can be achieved in which the resin materials softened or melted during welding mix together at a suitable degree, that is, junction can be achieved at a required junction strength.

The bonded portion 82 configured as described above has a higher bending strength than the air bags 81 and 101, and thus even when the air bags 81 and 101 are inflated and thus the air bags 81 and 101 are deformed, deformation of the bonded portion 82 is suppressed. As a result, the stress occurring in the bonding layer 8 between the curler 5 and the bonded portions 82 and 104 is stress in the tensile direction. Thus, in addition to the effects of the bonded portion 82 described above, the blood pressure measurement device 1B can further suppress the peeling between the curler 5 and the cuff structure 6. Additionally, when the resin material of the bonded portion 82 is similar to the resin material of the sheet member 86, the bonded portion 82 and the sheet member 86 can be suitably welded.

For example, the timings when the first on-off valve 16A and the second on-off valve 16B are opened and closed during blood pressure measurement of the blood pressure measurement device 1 are not limited to the timings in the examples described above, and can be set as appropriate. Additionally, although the example has been described in which the blood pressure measurement device 1 performs blood pressure measurement by calculating the blood pressure with the pressure measured during the process of pressurizing the palm-side cuff 71, no such limitation is intended and the blood pressure may be calculated during the depressurization process or during both the pressurization process and the depressurization process.

In addition, in the example described above, the configuration has been described in which the air bag 81 is formed by each of the sheet members 86, but no such limitation is intended, and for example, the air bag 81 may further include any other configuration in order to manage deformation and inflation of the palm-side cuff 71, for example.

Additionally, in the examples described above, the configuration is described in which the back plate 72 includes the plurality of grooves 72a, but no such limitation is intended. For example, for management of the likelihood of deformation and the like, the number, the depth, and the like of the plurality of grooves 72a may be set as appropriate, and the back plate 72 may be configured to include a member that suppresses deformation.

Furthermore, in the example described above, the blood pressure measurement device 1 has been described using an example of a wearable device attached to the wrist 200, but no such limitation is intended. For example, the blood pressure measurement device may be a blood pressure measurement device 1C wrapped around the upper arm to measure the blood pressure. Hereinafter, as a fourth embodiment, the blood pressure measurement device 1C will be described using FIG. 21. Note that components in the present embodiment that are similar to the corresponding components of the blood pressure measurement device 1 according to each embodiment described above are denoted by the same reference signs in the description, and descriptions and illustrations of these components are omitted as appropriate.

For example, as illustrated in FIGS. 21 to 23, the blood pressure measurement device 1C in the fourth embodiment includes a device body 3C and a cuff structure 6C. The device body 3C includes, for example, a case 11C, the display unit 12, the operation unit 13, the pump 14, the flow path unit 15, the on-off valves 16, the pressure sensors 17, the power supply unit 18, and the control substrate 20. As illustrated in FIG. 23, the device body 3C includes one of each of the pump 14, the on-off valves 16, and the pressure sensors 17.

The case 11C is constituted, for example, in a box shape. The case 11C includes an attachment portion 11a that fixes the cuff structure 6C. The attachment portion 11a is an opening provided in a back surface of the case 11C, for example.

As illustrated in FIGS. 21 to 23, the cuff structure 6C includes a curler 5C constituted by a thermoplastic resin material, a pressing cuff 71C provided on the living body side of the curler 5C and constituted by a thermoplastic resin material, and a bag-like cover body 76 inside which the curler 5C and the pressing cuff 71C are disposed and which includes a cloth or the like. The cuff structure 6C is wrapped around the upper arm.

The curler 5C includes a protruding portion 5c fixed to the attachment portion 11a, for example.

The pressing cuff 71C includes an air bag 81C, the bonded portion 82 provided in the air bag 81C, and a tube provided to the air bag 81C and fluidly connected to the flow path unit 15. The pressing cuff 71C is housed in the bag-like cover body 76 together with the curler 5C, and is joined to the inner surface of the curler 5C by thermal welding.

Each of the air bags 81C is constituted in a rectangular shape that is long in one direction. The air bag 81C is constituted, for example, by combining two sheet members 86 that are long in one direction, and thermally welding edges of the sheet members 86. As a specific example, the air bag 81C includes a first sheet member 86a and a second sheet member 86b in this order from the living body side. the second sheet member 86b constitutes the air bag 81C along with the first sheet member 86a, as illustrated in FIG. 22.

With such a blood pressure measurement device 1C, the bonded portion 82 welded to the air bag 81C is bonded to the inner circumferential surface of the curler 5C with the bonding layer 8 in between to join the curler 5C and the pressing cuff 71C.

Like the blood pressure measurement device 1 according to the first embodiment described above, the blood pressure measurement device 1C configured as described above can be miniaturized and can stably perform highly accurate blood pressure measurement for a long period of time.

In other words, the embodiments described above are merely examples of the present invention in all respects. Of course, various modifications and variations can be made without departing from the scope of the present invention. Thus, specific configurations in accordance with an embodiment may be adopted as appropriate at the time of carrying out the present invention.

Note that the present invention is not limited to the embodiment, and various modifications can be made in an implementation stage without departing from the gist. Further, embodiments may be carried out as appropriate in a combination, and combined effects can be obtained in such case. Further, the various inventions are included in the embodiment, and the various inventions may be extracted in accordance with combinations selected from the plurality of disclosed constituent elements. For example, in a case where the problem can be solved and the effects can be obtained even when some constituent elements are removed from the entire constituent elements given in the embodiment, the configuration obtained by removing the constituent elements may be extracted as an invention.

REFERENCE SIGNS LIST 1, 1A, 1B, 1C Blood pressure measurement device
3, 3C Device body
4 Belt 5, 5C Curler
5c Protruding portion
6, 6C Cuff structure
7 Fluid circuit
7a First flow path
7b Second flow path
7c Third flow path
8 Bonding layer
11, 11C Case
11a Attachment portion
12 Display unit
13 Operation unit
14 Pump
15 Flow path unit
16 On-off valve
16A First on-off valve
16B Second on-off valve
17 Pressure sensor
17A First pressure sensor
17B Second pressure sensor
18 Power supply unit
19 Vibration motor
20 Control substrate
31 Outer case
31a Lug
31b Spring rod
32 Windshield
33 Base
35 Back lid
35a Screw
41 Button
42 Sensor
43 Touch panel
51 Substrate
52 Acceleration sensor
53 Communication unit
54 Storage unit
55 Control unit
56 Main CPU
57 Sub-CPU
61 First belt
61a First hole portion
61b Second hole portion
61c Buckle
61d Frame body
61e Prong
62 Second belt
62a Small hole
62b Third hole portion
71 Palm-side cuff (cuff)
71C Pressing cuff
72 Back plate
72a Groove
73 Sensing cuff
74 Back-side cuff (cuff)
76 Bag-like cover body
81, 81C Air bag (bag-like structure)
82 Bonded portion
82 Second bonded portion
82a Second member
82A First bonded portion
82B Bonded portion
86 Sheet member
86a First sheet member
86b Second sheet member
86b1 Opening
86c Third sheet member
86c1 Opening
86d Fourth sheet member
91 Air bag (bag-like structure)
92 Tube
93 Connection unit
96 Sheet member
96a Fifth sheet member
96b Sixth sheet member
101 Air bag (bag-like structure)
102 Tube
103 Connection portion
104 Bonded portion (second bonded portion)
104a Second member
104A Bonded portion (first bonded portion)
104B Bonded portion
106 Sheet member
106a Seventh sheet member
106b Eighth sheet member
106b1 Opening
106c Ninth sheet member
106c1 Opening
106d Tenth sheet member
106d1 Opening
106e Eleventh sheet member
106e1 Opening
106f Twelfth sheet member
106f1 Opening
106g Thirteenth sheet member
106g1 Opening
106h Fourteenth sheet member
106h1 Opening
106i Fifteenth sheet member
106i1 Opening
106j Sixteenth sheet member
106j1 Opening
106k Seventeenth sheet member
106k1 Opening
106l Eighteenth sheet member
200 Wrist
210 Artery

The invention claimed is:

1. A blood pressure measurement device comprising:
a curler curving in such a manner as to follow along a circumferential direction of a wrist and formed with a first end and a second end spaced apart from each other;
a cuff formed of a resin material, the cuff including one bag-like structure or a plurality of bag-like structures stacked on one another and a bonded portion being bonded to the curler, each of the one bag-like structure or the plurality of bag-like structures being formed by welding two sheet members and configured to be inflated with a fluid, and the bonded portion being welded to one of the two sheet members disposed on a curler side of the one bag-like structure or one of the plurality of bag-like structures at a position closer to a center of the one bag-like structure or the one of the plurality of bag-like structures than edge portions where the two sheet members of the one bag-like structure or the one of the plurality of bag-like structures are welded together; and
a bonding layer bonding the curler and the bonded portion, wherein
the bonded portion is a sheet member integrally welded to the one of the two sheet members disposed on the curler side of the one bag-like structure or the one of the plurality of bag-like structures.

2. The blood pressure measurement device according to claim 1, wherein the bonded portion has a higher bending stress than the one of the two sheet members disposed on the curler side of the one bag-like structure or the one of the plurality of bag-like structures.

3. A blood pressure measurement device comprising:
a curler curving in such a manner as to follow along a circumferential direction of a wrist and formed with a first end and a second end spaced apart from each other;
a cuff formed of a resin material, the cuff including one bag-like structure or a plurality of bag-like structures stacked on one another and a bonded portion being bonded to the curler, each of the one bag-like structure or the plurality of bag-like structures being formed by welding two sheet members and configured to be inflated with a fluid, and the bonded portion being welded to one of the two sheet members disposed on a curler side of the one bag-like structure or one of the plurality of bag-like structures at a position closer to a center of the one bag-like structure or the one of the plurality of bag-like structures than edge portions where the two sheet members of the one bag-like structure or the one of the plurality of bag-like structures are welded together; and
a bonding layer bonding the curler and the bonded portion, wherein
the bonded portion is formed by two sheet members welded together to form a bag-like structure, the bag-like structure formed by the two sheet members of the bonded portion being smaller than the one bag-like structure or the one of the plurality of bag-like structures, and the bonded portion being integrally welded to the one of the two sheet members disposed on the curler side of the one bag-like structure or the one of the plurality of bag-like structures.

4. A blood pressure measurement device comprising:
a curler curving in such a manner as to follow along a circumferential direction of a wrist and formed with a first end and a second end spaced apart from each other;
a cuff formed of a resin material, the cuff including one bag-like structure or a plurality of bag-like structures stacked on one another and a bonded portion being bonded to the curler, each of the one bag-like structure or the plurality of bag-like structures being formed by welding two sheet members and configured to be inflated with a fluid, and the bonded portion being welded to one of the two sheet members disposed on a curler side of the one bag-like structure or one of the plurality of bag-like structures at a position closer to a center of the one bag-like structure or the one of the plurality of bag-like structures than edge portions where the two sheet members of the one bag-like structure or the one of the plurality of bag-like structures are welded together; and
a bonding layer bonding the curler and the bonded portion, wherein
the bonded portion includes a first bonded portion and a second bonded portion, the first bonded portion being formed by two sheet members welded together to form a bag-like structure, the bag-like structure formed by the two sheet members of the first bonded portion being smaller than the one bag-like structure or the one of the plurality of bag-like structures, the second bonded portion being a sheet member, and the first bonded portion being integrally welded to the one of the two sheet members disposed on the curler side of the one bag-like structure or the one of the plurality of bag-like structures and the second bonded portion being integrally welded to one of the two sheet members of the first bonded portion disposed on a curler side of the first bonded portion.

* * * * *